(12) United States Patent
Boesel et al.

(10) Patent No.: US 12,076,059 B2
(45) Date of Patent: Sep. 3, 2024

(54) PEDICLE SCREW RETRACTOR SYSTEM AND METHOD OF USE FOR SPINE SURGERY

(71) Applicants: Blake Boesel, North Palm Beach, FL (US); Robert P. Norton, Boca Raton, FL (US)

(72) Inventors: Blake Boesel, North Palm Beach, FL (US); Robert P. Norton, Boca Raton, FL (US)

( * ) Notice: Subject to any disclaimer, the term of this patent is extended or adjusted under 35 U.S.C. 154(b) by 374 days.

(21) Appl. No.: 17/172,230

(22) Filed: Feb. 10, 2021

(65) Prior Publication Data

US 2022/0249136 A1 Aug. 11, 2022

(51) Int. Cl.
| | |
|---|---|
| A61B 17/70 | (2006.01) |
| A61B 17/02 | (2006.01) |
| A61B 17/00 | (2006.01) |
| A61B 17/56 | (2006.01) |

(52) U.S. Cl.
CPC ...... *A61B 17/7079* (2013.01); *A61B 17/0218* (2013.01); *A61B 17/708* (2013.01); *A61B 2017/00477* (2013.01); *A61B 2017/0256* (2013.01); *A61B 2017/564* (2013.01); *A61B 17/7032* (2013.01)

(58) Field of Classification Search
CPC .............. A61B 17/72–7291; A61B 2017/0256
See application file for complete search history.

(56) References Cited

U.S. PATENT DOCUMENTS

| | | | | |
|---|---|---|---|---|
| 8,162,827 | B2 * | 4/2012 | Abdelgany | ........ A61B 17/0293 600/233 |
| 11,350,922 | B1 * | 6/2022 | Italiaie | ............... A61B 17/0206 |
| 2003/0083688 | A1 * | 5/2003 | Simonson | ............ A61B 17/025 606/191 |
| 2006/0069315 | A1 * | 3/2006 | Miles | .................... A61N 1/0551 600/219 |
| 2008/0058606 | A1 * | 3/2008 | Miles | ....................... A61B 1/32 600/214 |
| 2013/0190575 | A1 * | 7/2013 | Mast | ................... A61B 17/0206 600/219 |
| 2014/0066718 | A1 * | 3/2014 | Fiechter | ............. A61B 17/0206 600/214 |
| 2014/0135584 | A1 * | 5/2014 | Lee | .................... A61N 1/36017 600/219 |
| 2015/0018628 | A1 * | 1/2015 | Friedrich | ............. A61B 17/025 600/230 |
| 2017/0143323 | A1 * | 5/2017 | Cryder | ............... A61B 17/7032 |
| 2017/0333023 | A1 * | 11/2017 | Adams | ............... A61B 17/0218 |
| 2019/0090864 | A1 * | 3/2019 | Medeiros | ........... A61B 17/7032 |

(Continued)

*Primary Examiner* — Eduardo C Robert
*Assistant Examiner* — Steven J Cotroneo
(74) *Attorney, Agent, or Firm* — The Rapacke Law Group, P.A.; Andrew S. Rapacke

(57) ABSTRACT

A universal pair of pedicle screw-mounted retractor blades and locking shims configured for mounting over and locking onto the tower or extended top threaded post of a pair of adjacent pedicle screws pre-positioned in adjacent vertebrae. Each cylindrical retractor blade body has a proximal flange with an inverted post extending distally, configured for attachment to a handle or arm of a ratcheting retractor. The L-shaped locking shim is removably positioned along a grooved slot within the retractor blade body and temporarily locked into place within the tulip portion of the pedicle screw using a set screw.

18 Claims, 17 Drawing Sheets

(56) References Cited

U.S. PATENT DOCUMENTS

| | | | |
|---|---|---|---|
| 2019/0090979 A1* | 3/2019 | Medeiros | A61B 17/7082 |
| 2020/0187927 A1* | 6/2020 | Boesel | A61B 17/0206 |
| 2021/0169538 A1* | 6/2021 | Smith | A61B 17/7074 |
| 2021/0220009 A1* | 7/2021 | Heiges | A61B 17/0218 |
| 2022/0192645 A1* | 6/2022 | Peultier | A61B 17/025 |

* cited by examiner

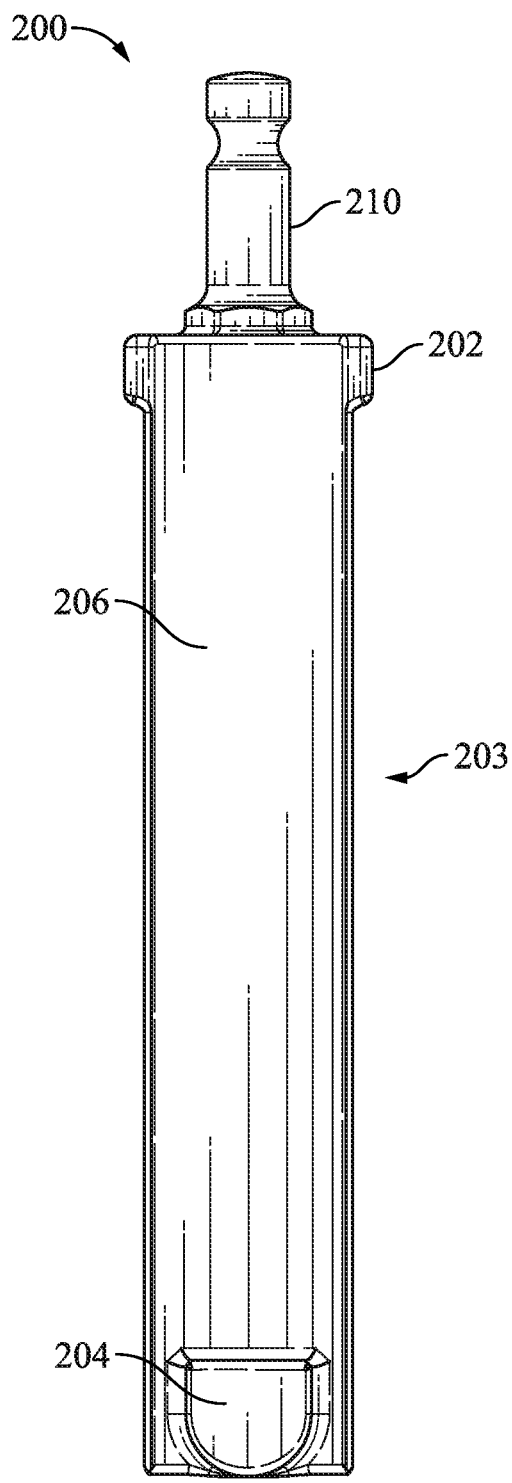
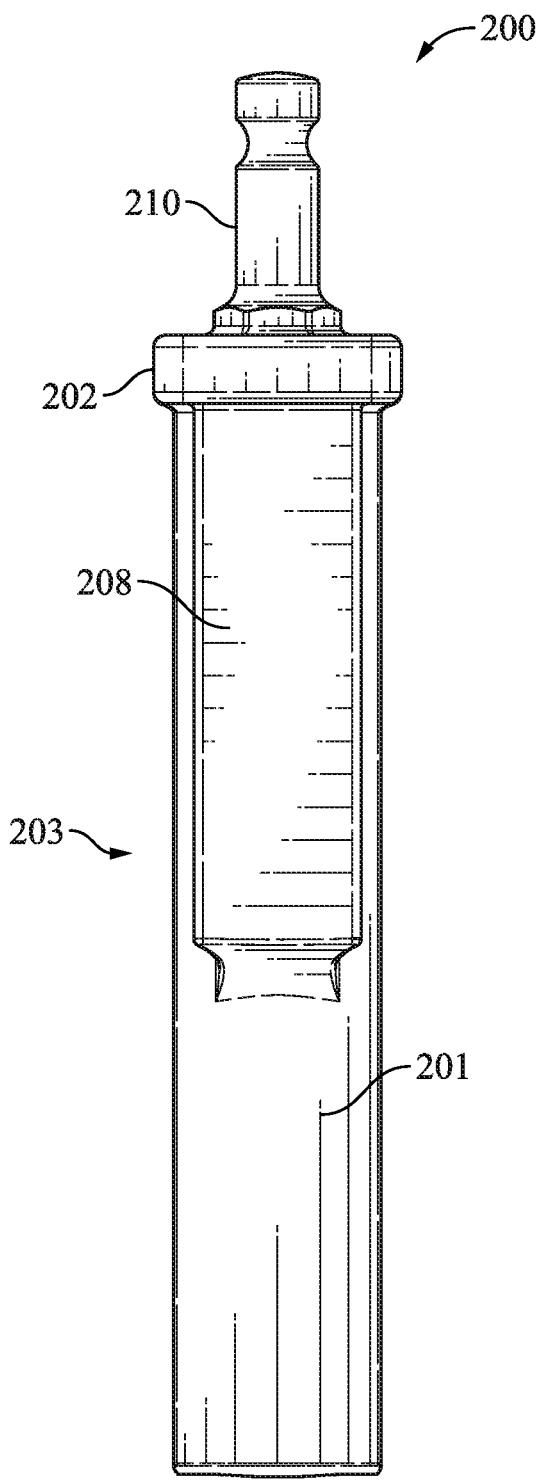
*FIG. 12*  *FIG. 13*

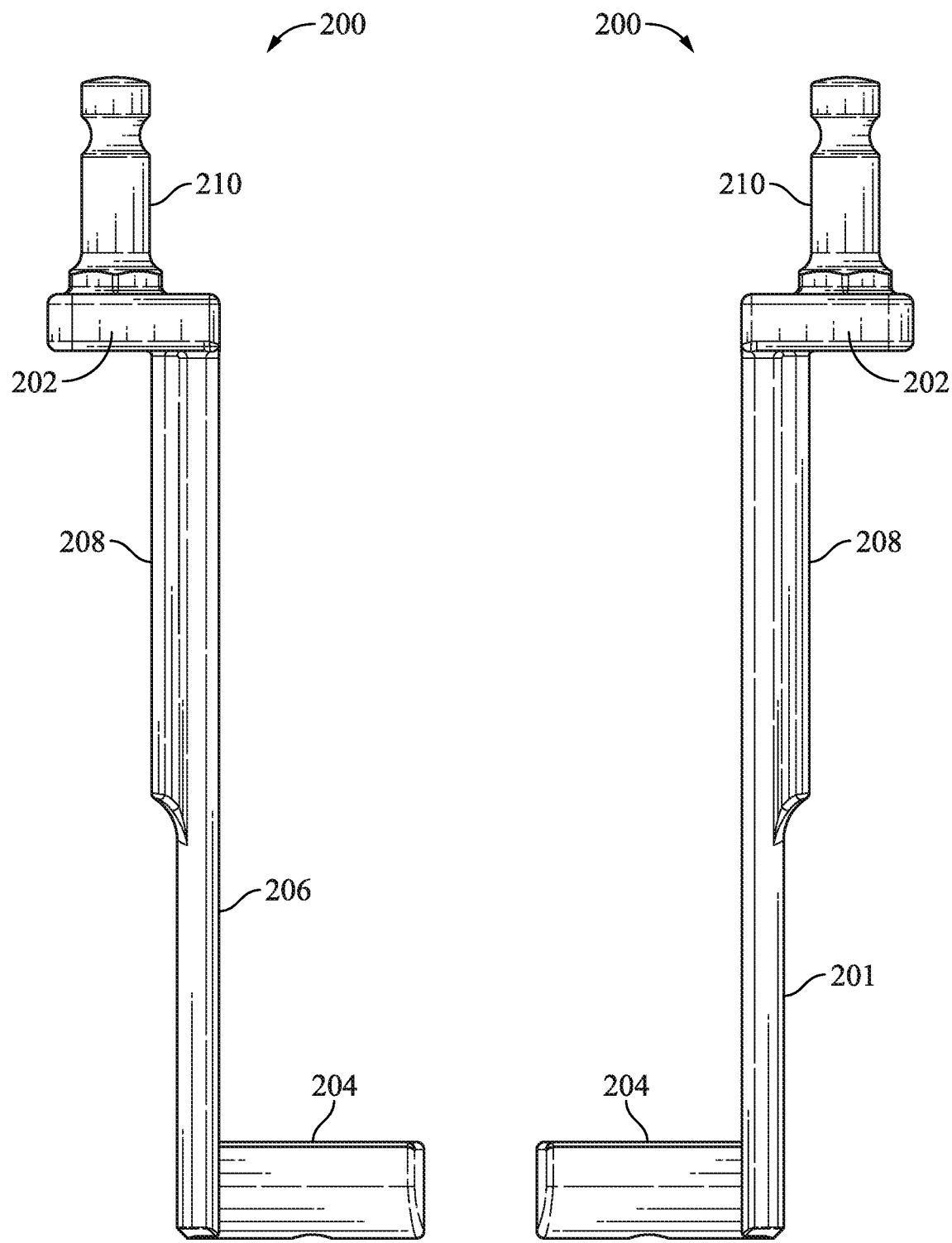
*FIG. 14*          *FIG. 15*

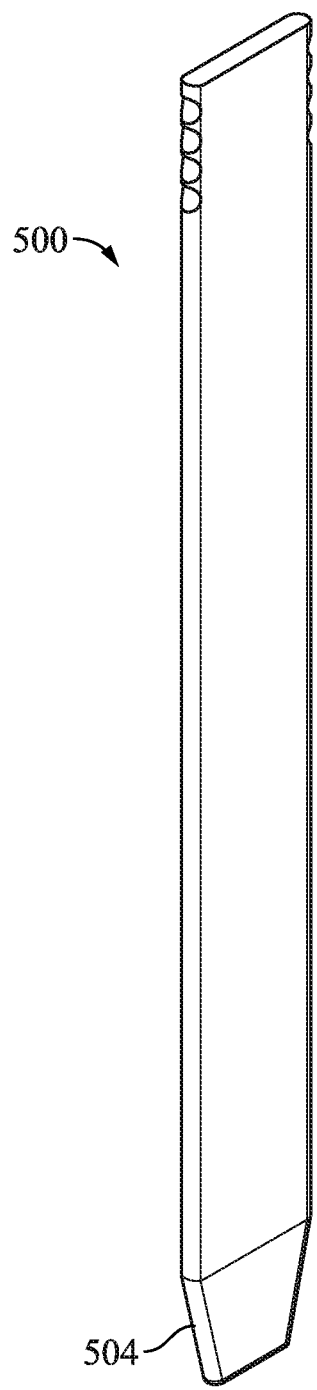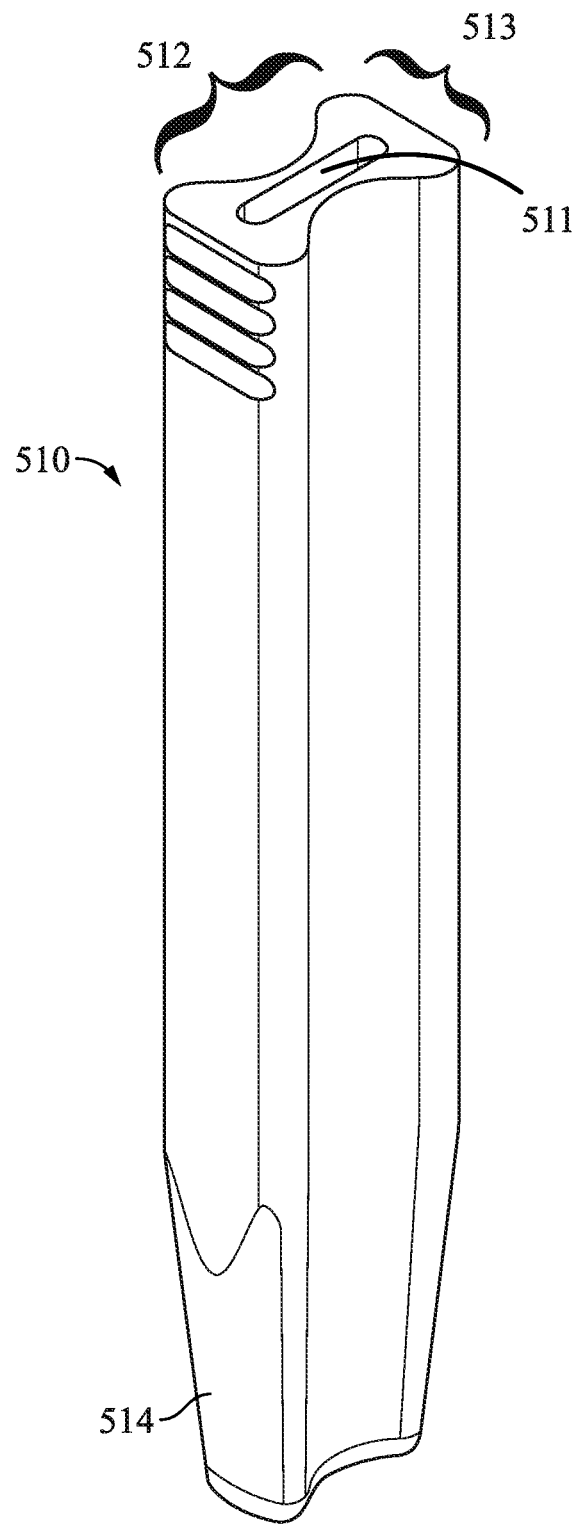
*FIG. 28*  *FIG. 29*

PEDICLE SCREW RETRACTOR SYSTEM AND METHOD OF USE FOR SPINE SURGERY

FIELD

The present disclosure relates to surgical instruments for spinal surgery; and more specifically, to a universal pedicle screw retractor system specifically designed for minimally invasive surgery of the spine.

BACKGROUND

Existing retractor systems provide limited control and less "feel" for the surgeon, taking away a skilled surgeon's ability to feel the resistance at the insertion blades or to rotate the blades independently affixed to the retractor arm, or to finely adjust the movement of the retractor blades. Additionally, existing retractor systems are limited to using screws that a manufactured specifically (and only) for the particular retractor system, which limits the usefulness of such retractor systems During a spinal surgery, one purpose for a retractor is to distract or separate ligaments and/or bone segments in a controlled fashion when performing, for example, a spinal fusion or disc replacement. But these procedures are not generally conducive to a minimally invasive approach due to the difficulty involved with passing a fusion rod between pedicle screws when the screw capture or tulip for each pedicle screw is typically 25 mm or more below the surface of the skin.

For at least the reasons above, there is a need for improved methods and devices that can be used for retracting tissue, ligaments, and bone segments in a controlled fashion when performing a spinal fusion or disc replacement, as well as to provide better access and visualization to the surgical site while minimizing trauma to soft tissue surrounding an incision. There is also a need for an improved retractor system having universal application; a retractor that can be used, for example, on any number of pedicle screws (e.g., 5.5 mm screw heads).

SUMMARY

In various embodiments, a universal pair of pedicle screw-mounted retractor blades and locking shims configured for mounting over and locking onto the tower or tulip (the extended top threaded post) of a pair of adjacent pedicle screws pre-positioned in adjacent vertebrae is provided. Each cylindrical retractor blade body can have a proximal flange with an inverted post extending distally, configured for attachment to a handle or arm of a ratcheting retractor. The L-shaped locking shim can be removably positioned along a grooved slot within the retractor blade tube and temporarily locked into place within the tulip portion of the pedicle screw using a set screw. The central working portal of each retractor blade tube can have at least a 20 mm inside diameter in each of the first and second bodies. In some embodiments, the L-shaped foot of the locking shim is configured to lock the retractor blade tube into any 5.5 mm pedicle screw head or tulip; the most common screw head "tulip" size used in spinal procedures.

In some embodiments, a unique inverted connection post is provided. The inverted connection post is designed to more easily attach and lock onto a distraction handle or arm of a distraction tool used to distract or separate adjacent vertebrae so a surgeon has adequate room to perform a fusion preparation of the disc space therebetween. In some embodiments, the inverted post provides distinct advantages to the flow of the surgical procedure and reduces cantilever stresses on the pedicle screws.

In some embodiments, a pedicle screw-mounted retractor system comprising a first and a second pedicle screw-mounted retractor blade body having a proximal and distal end, a proximal shoulder, an inside diameter, a first partially offset non-concentric outside diameter and a second partially concentric outside diameter; and a first and a second locking shim is provided. Each retractor blade body can comprise a longitudinal diametral tube configured with a proximal opening a distal opening and through bore. Each locking shim can comprise a leg, a distal L-shaped foot, an opposing proximal top flange projecting away from the distal L-shaped foot. Each said retractor blade body is configured for placement over and onto an extended tulip of a first and a second pedicle screw. The locking shim is configured for removable locking placement between the extended tangs of a pedicle screw tower of each of the first and a second pedicle screw, within each diametral retractor blade tube. Each pedicle screw is pre-positioned in a pair of adjacent caudal and cephalad vertebrae on the same side of the spine and configured for distracting the vertebrae.

In some embodiments, each retractor blade body can further comprise an alignment groove on the inside diameter configured to receive a mating alignment projection on the leg of each of the locking shims, forming a tower assembly when each locking shim is inserted into each retractor blade body.

In some embodiments, the locking shim can be releasably locked in place on each pedicle screw tower with a pedicle set screw, forming a retractor blade screw tower assembly.

In some embodiments, the system can comprise a proximal end flange extending perpendicularly on one side of each retractor blade body, comprising a first receptacle configured to receive the proximal top flange of the locking shim and a second receptacle configured to receive a post sub-assembly; and a post sub-assembly extending distally from the second receptacle. Each post sub-assembly is configured to lockably receive a handle or a mounting arm of a spinal joint retractor.

In some embodiments, each retractor blade body can comprise at least one visualization slot through one side of the retractor blade body (extending between the proximal end and the distal end). Said at least one visualization slot can be positioned diametrically opposite the side having the proximal flange.

In some embodiments, each retractor blade body further comprises an additional slot, on a side diametrically opposed to the at least one visualization slot, on the same side as the proximal end flange, along the distal half of the retractor blade tube and configured to accommodate the passage of a spinal connecting rod therethrough. In some embodiments, the distal additional slot extends from the distal end of each diametral retractor blade tube to a point approximately 50% of the length to the proximal end.

In some embodiments, each retractor blade body can comprise a tapered exterior configuration at or about the distal end of the tube body.

In some embodiments, the distracting of the vertebrae with the pedicle screws is performed with the retractor blade screw tower assemblies securely positioned over and locked onto the pedicle screws while maintaining the pedicle screws parallel with the tubes during a distraction maneuver with a pedicle-based retractor attached to the distally extending post sub-assemblies.

In some embodiments, the alignment groove on the inside diameter each retractor blade body can be configured as: a v-groove; an undercut groove; a dovetail; a through dovetail; a half-blind dovetail; or a sliding dovetail. The alignment projection on the leg of each of the locking shims can be configured to slidably mate with the alignment groove and prevent disassociation of the shim from the inside diameter of the retractor blade body.

In some embodiments, the proximal top flange of each locking shim comprises an attachment feature configured to receive an inserter/extractor tool. Said attachment feature can comprise: a threaded hole; a post; a threaded post; a snap-detent; a bayonet attachment; or a compression-type fitting.

In some embodiments, the first partially offset non-concentric outside diameter comprises an approximately semi-circular non-concentric offset diameter for one half of the outside diameter and the second partially concentric outside diameter comprises an approximately semi-circular concentric outside diameter for the other half of the outside diameter.

In some embodiments, each said distally extending post sub-assembly can comprise a spring-loaded locking mechanism for engaging the handle or the mounting arm of a spinal joint retractor. Said spring-loaded locking mechanism can engage with an engagement driver to activate and release the mechanism.

In some embodiments, the system comprises a set of MIS spinal dilators sized to dilate an incision between the pair of pedicle screws. Each retractor blade body of the pedicle screw-mounted retractor system can be configured to pass over and attach onto each pedicle screw tower positioned in the adjacent vertebrae and the dilators positioned therebetween configured to increase the size of an MIS surgical working portal therebetween. The set of MIS spinal dilators can comprise: a flat "tongue depressor" dilator, and a "peanut" dilator, configured with a slidably matching through-slot within its longitudinal length configured to allow the peanut dilator to slide over the flat tongue depressor dilator.

In various embodiments, a method of distracting a pair of adjacent vertebrae for a TLIF procedure is provided. The method can comprise: creating a MIS incision for a central working MIS portal for a spinal TLIF procedure; inserting dilators in the central working MIS portal to expand and open soft tissue to visualize and verify position and anatomy; inserting a pair of pedicle screws with threaded towers and/or extended tangs, one in each pedicle, in adjacent caudal and cephalad vertebra, on the ipsilateral side of the spine where the TLIF procedure is being performed; providing a first and a second pedicle screw-mounted retractor blade body; placing each retractor blade body over and onto each of the pedicle screw towers, flush to the pedicle. Each retractor blade tube can comprise an inside diameter with a retaining alignment groove, a first partially offset non-concentric outside diameter and a second partially concentric outside diameter, said second partially concentric outside diameter being configured with a visualization slot extending from a proximal end to a distal end, said visualization slots positioned diametrically facing each other when the pair of retractor blade tubes are placed over the pedicle screws, and each retractor blade body having a proximal end flange extending perpendicular on a side opposite the visualization slot, with an inverted post sub-assembly extending distally therefrom and positioned diametrically opposed to each other when the retractor blade bodies are placed over the pedicle screws. Each retractor blade tube can comprise a second distal slot on a diametral side opposite the visualization slot, along the distal half of the retractor blade tube comprising the first partially offset non-concentric outside diameter. The method can further comprise inserting a locking shim with a mating retaining alignment projection within the retractor blade tube. A protruding distal foot of said locking shim can be configured for placement between extended threaded towers or extended tangs of each tower of each of the first and a second pedicle screw. The method can further comprise inserting a pedicle set screw into each of the extended threaded towers or extended tangs of each of the first and a second pedicle screws, removably locking each locking shim in place within each pedicle screw tower, securing the retractor blade assembly to each pre-positioned ipsilateral pedicle screw, forming a retractor blade screw tower assembly; attaching a spinal pedicle-based retractor to each distally extending inverted post; and performing a distraction maneuver. The distraction of the vertebrae spacing occurs when the cylindrical retractor blade bodies are distracted in caudal and cephalad directions. The method can further comprise removing the dilators, and leaving the retractor blade bodies in place to visualize through the central working MIS portal to verify the position and anatomy.

In some embodiments, at any time following the insertion of the pedicle screws on the ipsilateral side of the spine, the method can further comprise inserting a second pair of pedicle screws with threaded towers or extended tops or tangs with threaded posts, one in each pedicle, in adjacent caudal and cephalad vertebra, on the contralateral side of the spine where the TLIF procedure is being performed.

In some embodiments, following the distraction maneuver, a TLIF procedure can be performed. In some embodiments, following the TLIF procedure, the method can further comprise: releasing the distraction maneuver with the pedicle-based retractor to allow compression of a TLIF-treated disc space; removing the set screws from each of the first and a second pedicle screws; removing the locking shim from each of the first and a second retractor blade screw tower assembly; inserting spinal rods through the second distal slots of the retractor blade tubes and the pedicle screw towers between the adjacent caudal and cephalad vertebra on the ipsilateral side of the spine; inserting a pedicle set screw into each of the extended threaded tangs of each of the first and a second pedicle screws on the ipsilateral side of the spine, locking each spinal rod in place within each pedicle screw; inserting spinal rods between the adjacent caudal and cephalad vertebra on the contralateral side of the spine; and inserting a pedicle set screw into each of the extended threaded tangs of each of the first and a second pedicle screws on the contralateral side of the spine, locking each spinal rod in place within each pedicle screw.

In some embodiments, at any time following the releasing the distraction maneuver, the method can further comprise removing the pedicle-based retractor from each retractor blade body; and removing each retractor blade body from the pedicle screws in the adjacent caudal and cephalad vertebra.

In various embodiments, a pedicle screw-mounted retractor system is provided. The system can comprise a first and a second pedicle screw-mounted retractor blade body having a proximal and distal end, a proximal shoulder, an inside diameter, a first partially offset non-concentric outside diameter and a second partially concentric outside diameter; and a first and a second locking shim. Each retractor blade body can comprise a longitudinal diametral tube configured with a proximal opening, a distal opening, and through bore. Each locking shim can comprise a leg, a distal L-shaped foot with a centrally positioned guidewire hole, an opposing proximal top flange projecting away from the distal L-shaped foot. Each retractor blade body can be configured for placement over and onto an extended tulip of a first and a second pedicle screw. The locking shim, with the centrally positioned guidewire hole in the L-shaped foot, can be configured for guiding a partially assembled retractor blade assembly over a pre-positioned guidewire that was used to position a canulated pedicle screw in the facet of a vertebrae, wherein, once positioned within the tulip of the pre-positioned pedicle screw, each said locking shim can be configured for removable locking placement with a set screw between the extended tangs of said tulip of each of the first and a second pedicle screw, within each diametral retractor blade tube, and wherein each pedicle screw is pre-positioned in a pair of adjacent caudal and cephalad vertebrae on the same side of the spine and configured for distracting the vertebrae. In some embodiments, the pedicle screw-mounted retractor system is configured for placement on the ipsilateral side of the spine where a TLIF procedure is being performed. In some embodiments, the guidewire hole in the L-shaped foot of the locking shim is approximately 3.2 mm in diameter.

In some embodiments, the system can comprise a proximal end flange extending perpendicularly on one side of each retractor blade body, comprising a first receptacle configured to receive the proximal top flange of the locking shim and a post sub-assembly extending distally from the second receptacle. Each said post sub-assembly can be configured to lockably receive a handle or a mounting arm of a spinal joint retractor.

In some embodiments, the distally extending post sub-assembly can comprise a spring-loaded mechanism comprising a locking feature configured to extend through and rotationally lock onto or into a mating receiving aperture of a handle or a mounting arm of a spinal joint retractor to temporarily hold the pedicle screw-mounted retractor blade body for a retraction step in a spinal procedure. In some embodiments, the locking feature comprises a T-bar, a hook, an L-shaped foot, a bayonet connection or a ball detent.

The foregoing general summary is intended to provide an overview or framework for understanding the nature and character of the embodiments disclosed herein. This summary is not intended to identify essential inventive concepts of the claimed subject matter or limit the scope of the claimed subject matter. Additional features and advantages of the embodiments disclosed herein will be set forth in the detailed description that follows, and in part will be clear to those skilled in the art from that description or recognized by practicing the embodiments described herein, including the detailed description that follows, the claims, and the appended drawings.

BRIEF DESCRIPTION OF THE DRAWINGS

A complete understanding of the present embodiments and the advantages and features thereof will be more readily understood by reference to the following detailed description, appended claims, and accompanying drawings, wherein:

FIG. 12 is a front view of the locking shim of FIG. 11;

FIG. 13 is a rear view of the locking shim of FIG. 11;

FIG. 14 is a left side view of the locking shim of FIG. 11;

FIG. 15 is a right-side view of the locking shim of FIG. 11;

FIG. 28 is an isometric view of an optional dilator used in the method of performing a TLIF procedure with the subject inverted pedicle retractor assembly, in accordance with embodiments disclosed herein; and FIG. 29 is an isometric view of an optional dilator used with the dilator of FIG. 28.

Figure 1A:
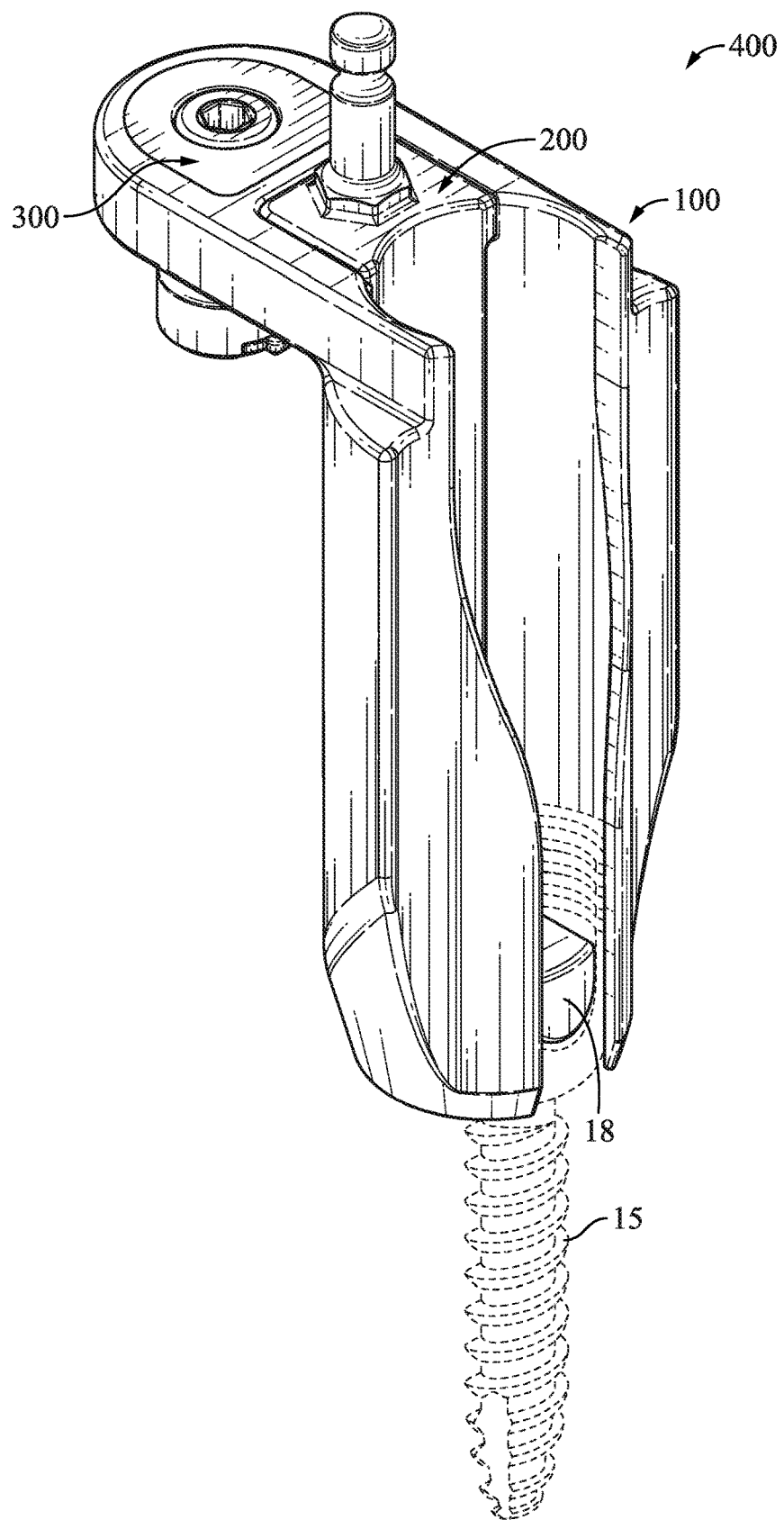
FIG. 1A is a perspective view of an assembled, inverted pedicle retractor assembly, in accordance with embodiments disclosed herein.

The drawings are not necessarily to scale, and certain features and certain views of the drawings may be shown exaggerated in scale or in schematic in the interest of clarity and conciseness.

DETAILED DESCRIPTION

Reference will now be made in detail to the exemplary embodiment(s), examples of which is/are illustrated in the accompanying drawings. Whenever possible, the same reference numerals will be used throughout the drawings to refer to the same or like parts.

Before describing the exemplary embodiments, it is noted the embodiments reside primarily in combinations of components and procedures related to the apparatus. Accordingly, the apparatus components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

The specific details of the various embodiments described herein are used for demonstration purposes only, and no unnecessary limitation or inferences are to be understood therefrom. Furthermore, as used herein, relational terms, such as "first" and "second," "top" and "bottom," and the like, may be used solely to distinguish one entity or element from another entity or element without necessarily requiring or implying any physical or logical relationship, or order between such entities or elements.

In various embodiments, the present disclosure provides a versatile, universal pair of pedicle screw-mounted retractor blades and locking shims configured for mounting over and locking onto the tower or extended top threaded tulip of a pair of adjacent pedicle screws pre-positioned in adjacent vertebrae when performing a minimally invasive vertebral fusion procedure.

Fusion surgery of the spine can be approached from the front, the side, or the back. A number of technological advances have allowed fusion surgery to be performed using minimally invasive techniques in select cases. The benefits of this type of surgery have resulting in smaller surgical incisions, meaning less trauma to the soft tissues, lower levels of blood loss and ultimately, reduced recovery time since the body has less work to do in order to recover. A further benefit is reduced scarring at the surgical site.

One such surgery, which was routinely done as a full-open anterior procedure has now been modified to an Anterior Lumbar Interbody Fusion or ALIF. Anterior lumbar interbody fusion (ALIF) is a type of spinal fusion that utilizes an anterior (front, that is through the abdominal region) approach to fuse the lumbar spine bones together. Most commonly these involve the lumbar L3, L4, L5 and sacrum Si vertebrae. Interbody fusion means the intervertebral disc is removed and replaced with a bone, plastic or metal spacer, in this case using an anterior approach. The anterior technique is often favored when multiple spinal levels are being fused and multiple discs need to be removed. ALIF may be performed in conjunction with or without a posterior decompression (laminectomy) and/or instrumentation (use of metal screws/rods). The anterior ALIF approach is also ideal when only one spinal level is fused and a posterior decompression and/or instrumentation are not required. Although the anterior lumbar ALIF approach involves retracting (moving out of the way, temporarily) large blood vessels (aorta, vena cava) and the intestines, there is a wide exposure of the intervertebral disc without retraction of the spinal nerves and neurologic structures (and therefore, a decreased risk of neurologic injury). ALIF is commonly performed for a variety of painful spinal conditions, such as spondylolisthesis and degenerative disc disease, among others.

Surgeons routinely perform minimally invasive fusion of the lumbar spine from the side (LLIF, XLIF or DLIF surgery) as well as from the back (TLIF or PLIF surgery). These less invasive techniques can reduce infection rates and blood loss and lead to a faster recovery.

Lumbar lateral interbody fusion (LLIF), or extreme lateral interbody fusion (XLIF) or direct lateral interbody fusion (DLIF) are names for essentially the same type of procedure, each having the same lateral approach to the spine. LLIF, XLIF or DLIF are minimally invasive procedures performed through the side of the body to treat spinal disorders and reduce long-term back or leg pain that has not responded to other treatments, such as steroid injections, physical therapy and pain medication. LLIF, XLIF or DLIF procedures differ from traditional procedures because the surgeon accesses the space between each spinal disc from the patient's side, rather than from the front or back, sparing major back muscles, bones and ligaments. During these lateral approach procedures, surgeons work in areas that are close to nerves on the spinal column. To prevent nerve damage, nerve monitoring, called electromyography or EMG, is used that provides surgeons with real-time information about nerve position relative to his or her instruments.

The lateral fusion (LLIF/XLIF/DLIF) has the benefit of obtaining excellent fusion potential through a minimally invasive approach. The disc is removed and replaced with a large spacer made of allograft bone or a synthetic material, (typically PEEK or titanium), and bone graft (or substitute such as bone morphogenic protein (BMP)). The size of the spacers inserted thru the lateral approach is typically twice the size of spacers inserted from the back (TLIF or PLIF approach). The larger spacers provide increased stability, increase the disc height in order to restore alignment, and increase the chance of successful fusion. Pedicle screws, which may be used for additional stability, are inserted into the disc space in order to stabilize the motion segment (e.g., L4-L5 disc segments) and increase fusion rate. Surgeons may also insert pedicle screws under three-dimensional computer navigation which increases the accuracy and safety of the procedure.

Advantages of LLIF, XLIF or DLIF include: (i) less surgery time because LLIF, XLIF or DLIF can be completed in as little as an hour, reducing the time the patient is in surgery and under anesthesia; (ii) less blood loss and scarring because minimally invasive procedures result in less tissue disruption and reduced blood loss; (iii) less pain because the surgeon accesses the intervertebral disc space from the patient's side, LLIF, XLIF or DLIF does not disrupt sensitive back muscles, bones or ligaments (many patients are able to walk the same day after surgery); (iv) shorter hospital stay (e.g., LLIF, XLIF or DLIF requires only an overnight hospital stay, compared to several days of immobility and hospitalization after traditional procedures); and (v) quicker return to normal activity (patients usually walk the day of surgery, although full recovery takes a few months, compared to six months or more for traditional procedures).

Posterior lumbar interbody fusion (PLIF) and transforaminal lumbar interbody fusion (TLIF) are two types of spinal fusion procedures that utilize a posterior (back area incision) approach to fuse the lumbar spine bones together. The posterior technique is often favored when one or two spinal levels are being fused in conjunction with a posterior decompression (laminectomy) and instrumentation (use of metal screws/rods). PLIF and TLIF procedures are commonly performed for a variety of painful spinal conditions, such as spondylolisthesis and degenerative disc disease, among others. The traditional PLIF procedure involves placing two small bone graft spacers, with gentle retraction of the spinal nerves and neurologic structures, one graft on each side of the interbody space (right and left). As with any spinal fusion surgery, a posterior lumbar interbody fusion (PLIF) involves adding bone graft to an area of the spine to set up a biological response that causes the bone to grow between the two vertebral elements and thereby stop the motion at that segment. Unlike the posterolateral gutter fusion, the PLIF achieves spinal fusion in the low back by inserting a cage made of either allograft bone or synthetic material (PEEK or titanium) directly into the disc space. A PLIF procedure is often supplemented by a simultaneous posterolateral spine fusion surgery.

Doing a PLIF surgery has the advantage that it can provide anterior fusion of the disc space without having a second incision as would be necessary with an anterior/posterior spine fusion surgery. However, it has some disadvantages, including: (i) not as much of the disc space can be removed with a posterior approach (from the back); (ii) an anterior approach (an ALIF, from the front) provides for a much more comprehensive evacuation of the disc space and this leads to increase surface area available for a fusion; (iii) a larger spinal implant can be inserted from an anterior approach, which provides for superior stabilization; (iv) in cases of spinal deformity (e.g. isthmic spondylolisthesis) a posterior approach alone is more difficult to reduce the deformity; and (v) there is a small but finite risk that inserting a cage posteriorly will allow it to retro pulse back into the canal and create neural compression.

PLIF surgery has a higher potential for solid fusion rates than posterolateral fusion rates because the bone is inserted into the anterior portion (front) of the spine. Bone in the anterior portion fuses better because there is more surface area than in the posterolateral gutter, and also because the bone is under compression. Bone in compression heals better because bone responds to stress (Wolff's law), whereas bone under tension (posterolateral fusions) does not see as much stress.

Transforaminal lumbar interbody fusion (TLIF) involves placing only one bone graft spacer in the middle of the interbody space, without retraction of the spinal nerves. In recent years, many surgeons have begun to use the TLIF procedure in preference to the PLIF. A TLIF can accomplish the same goals as a PLIF procedure. However, in TLIF the surgeon inserts the bone graft into the disc space from the side. This results in the nerve roots being moved less during the procedure, as compared to a PLIF, and may reduce the risk of scarring or damaging the nerve roots.

In a typical posterior spine fusion, at least two vertebral bodies are rigidly connected via facet or pedicle screws implanted into the respective vertebral bodies wherein a construct can be formed using solid metal rods spanning the distance between the screws. In the recent past, this procedure was not generally conducive to a minimally invasive approach. The insertion of pedicle or facet screws is relatively straightforward and can be accomplished through a minimal incision. The difficulty arises upon the introduction of a length of rod into a small incision with extremely limited access and visibility. A single level fusion may require a 30-40 mm rod to be introduced into a 1 cm incision and a multilevel fusion may require a rod several inches long, or longer, to fit into a 1 cm incision, entering a capture space in the pedicle screw and bridging the distance to the next sequential pedicle screw 25-30 mm proximal in location. Further still, the screw capture is typically 25 mm or more below the surface of the skin. For this reason, it is important that the minimal incision be maintained in an open and accessible condition for introduction of the rod.

Retractor systems are used in a variety of different surgical procedures to provide a larger opening through a minimal soft tissue incision, through which a surgeon may better access the surgical site. In spinal surgeries, a retractor system is used to provide the surgeon with better access to the patient's spine. The opening created by the retractor system may enable the surgeon to insert specially designed surgical instruments into the body or enable better visualization of the surgical site. The retractor system not only provides the surgeon with better visibility deep in the surgical site and clearer views of the affected disc space in the spine, and clearer visibility of the pedicle, pedicle screws and vertebrae through the visibility slots, but also provides the surgeon with guided delivery channels for clearer passage of the spinal fusion rods between the tulip saddles of the pedicle screws through the combined delivery slot and rod passage slot on the opposite sides of each retractor blade body, followed by protected delivery of the locking screws used to tighten the fusion rods in place within each retractor blade body.

Additionally, the "inverted" connection post protruding from each retractor blade body shoulder, reduces the lever arm stresses, placing less stress on the pedicle screw shank and lowers the center of gravity of each retractor blade body during retraction, reducing the risk of tilting or otherwise twisting the affected vertebrae out of alignment during the retraction maneuver.

Further, it has been found that by having the connection post in the inverted position, attachment of a handle or retractor arm to the retractor blade is significantly easier when pressing the post (and retractor blade) down into the receiving hole of the handle or retractor arm while the retractor blade is attached to the pedicle screw, rather than pulling the retractor blade up into the receiving hole of the handle or retractor arm, without the potential for fracturing the screw or dislodging the tulip of the screw.

In various embodiments, a pedicle screw-mounted retractor system 10 is provided. In some embodiments, the system comprises a first and a second pedicle screw-mounted retractor blade body 100 having a proximal end 103 and distal end 105, a proximal shoulder 102, an inside diameter 106, a first partially offset non-concentric outside diameter 101a and a second partially concentric outside diameter 101b; and a first and a second locking shim 200; wherein each retractor blade body comprises a longitudinal diametral tube configured with a proximal opening a distal opening and through bore, wherein each locking shim comprises a leg 203, a distal L-shaped foot 204, an opposing proximal top flange 202 projecting away from the distal L-shaped foot, wherein each said retractor blade body is configured for placement over and onto an extended tulip of a first and a second pedicle screw 15, wherein the locking shim is configured for removable locking placement between the extended tangs (not shown) of a pedicle screw tower of each of the first and a second pedicle screw, within each diametral retractor blade tube, and wherein each pedicle screw is pre-positioned in a pair of adjacent caudal 20 and cephalad 30 vertebrae on the same side of the spine and configured for distracting the vertebrae.

In some embodiments of the pedicle screw-mounted retractor system 10, each retractor blade body 100 further comprises an alignment groove 108 on the inside diameter 106 configured to receive a mating alignment projection 208 on the leg of each of the locking shims, (forming an individual screw tower assembly 400) when each locking shim 200 and an inverted connection post sub-assembly 300 is inserted into each retractor blade body (and attached to pedicle screw tower with a pedicle set screw).

In some embodiments, the locking shim 200 can be releasably locked in place on each pedicle screw tower with a pedicle set screw (not shown), forming a retractor blade screw tower assembly 400. In some embodiments, the pedicle set screw also functions to secure the fusion rod.

In some embodiments, the system further comprises a proximal end flange 102 extending perpendicularly on one side (front side) of each retractor blade body, comprising a first receptacle or capture space 110 configured to receive the proximal top flange 208 of the locking shim and a second receptacle or thru-hole 112 to receive an inverted post sub-assembly 300; said post sub-assembly extending distally from the second receptacle, wherein each said post sub-assembly is configured to lockably receive a commercially available handle or a mounting arm of a spinal joint retractor.

In some embodiments, each retractor blade body further comprises at least one tapered visualization slot through one side (rear side) 116, 118b of the retractor blade body (extending between the proximal end 103 and the distal end 105), said at least one visualization slot positioned diametrically opposite the side having the proximal flange.

In some embodiments, each retractor blade body further comprises an additional slot, a rod passage notch 118a, on a side diametrically opposed to the at least one visualization slot, (the front side), on the same side as the proximal end flange, along the distal half of the retractor blade tube on the partially offset non-concentric front outside diameter 101a, and configured to accommodate the passage of a spinal connecting rod therethrough.

In some embodiments, the distal additional slot 118a extends from the distal end 105 of each diametral retractor blade tube to a point approximately 50% of the height 120 to the proximal end. In some embodiments, the distal additional slot 118a extends from the distal end 105 to a point approximately 35-65%, or 40-60%, or about 44%, 45%, 46%, 47%, 48%, 49%, 51%, 52%, 53%, 54%, 55%, or 56% of the height 120 to the proximal end.

In some embodiments, each retractor blade body further comprises a tapered exterior configuration 104 at or about the distal end 105 of the tube body 100.

In some embodiments, the alignment groove 108 on the inside diameter 106 each retractor blade body is configured to be: a v-groove; an undercut groove; a dovetail; a through dovetail; a half-blind dovetail; or a sliding dovetail; and wherein the alignment projection 208 on the leg of each of the locking shims 200 is configured to slidably mate with the alignment groove and prevent disassociation of the shim from the inside diameter of the retractor blade body.

In some embodiments, the first partially offset non-concentric outside diameter 101a comprises an approximately semi-circular non-concentric offset diameter for one half of the outside diameter and the second partially concentric outside diameter 101b comprises an approximately semi-circular concentric outside diameter for the other half of the outside diameter.

With reference now to FIGS. 1A-10, a pedicle screw-mounted retractor system 10 is illustrated comprising a first and a second pedicle screw-mounted retractor blade body 100, each blade body having a proximal end 103 and distal end 105, a proximal shoulder 102, an inside diametral thru-bore 106, a first partially offset non-concentric front outside diameter 101a and a second partially concentric rear outside diameter 101b. In some embodiments, the retractor blade body further comprises a shoulder flange capture 110 for receiving a locking shim shoulder flange 202, and a female dovetail capture groove 108 on the inside diametral thru-bore 106 for receiving and retaining a mating feature on the locking shim 200 and a corresponding dovetail abutment 122 on the on the major diameter 101a on the front of the retractor blade body. In some embodiments, the retractor blade body comprises a proximal-to-distal tapered rear visualization notch 116, 118b, a front rod passage notch 118a having a height 120 and a tapered distal end 104. Still further the proximal shoulder 102 comprises a thru-hole capture diameter 112, having a stepped counter-seat 114 configured to receive and capture an inverted connection post sub-assembly 300.

Figure 1B:
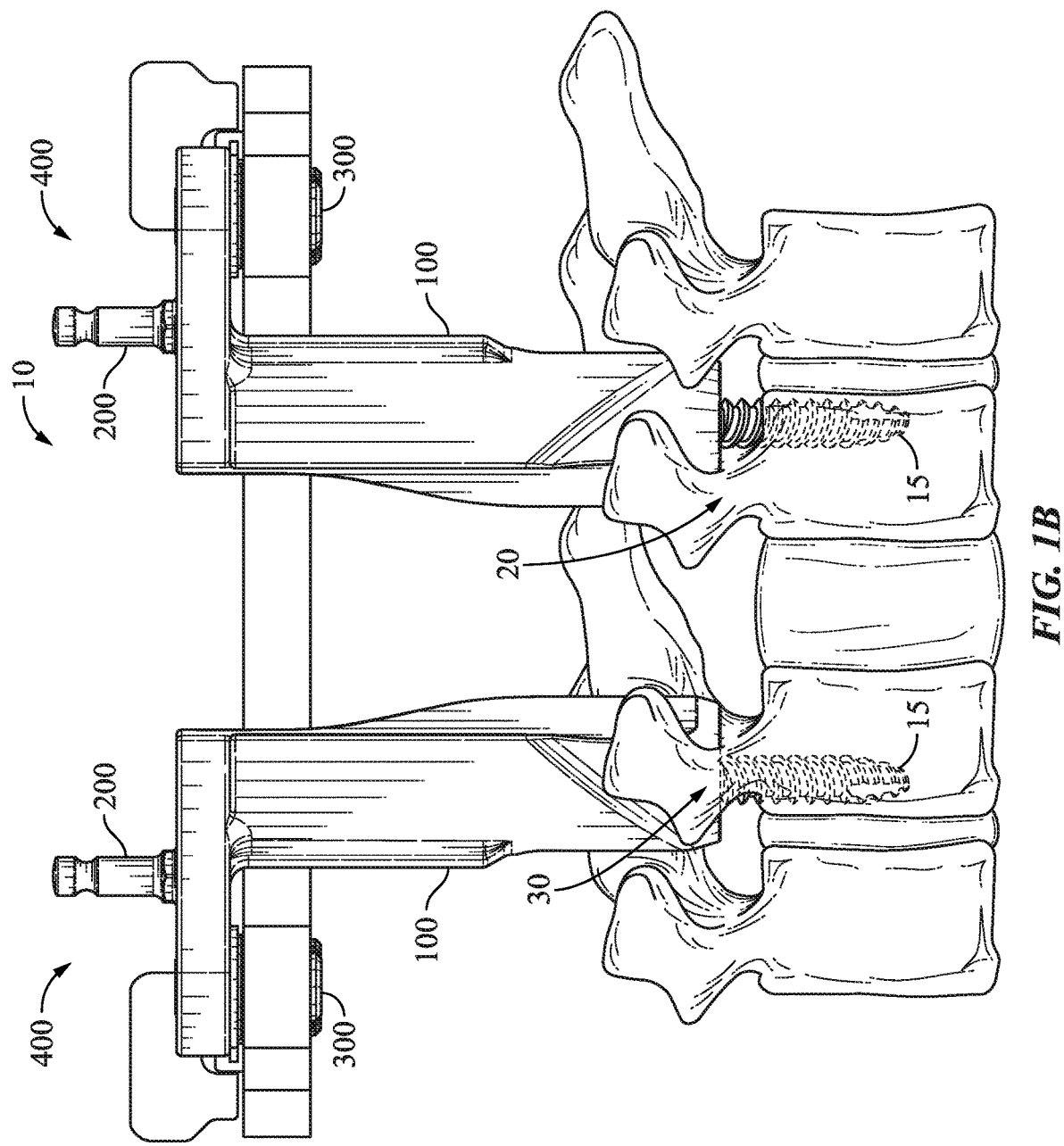
FIG. 1B is a side environmental view of an inverted pedicle retractor assembly system with the retractor blades placed in adjacent vertebrae and connected with a retractor to the inverted connection posts, in accordance with embodiments disclosed herein.
Figure 2:
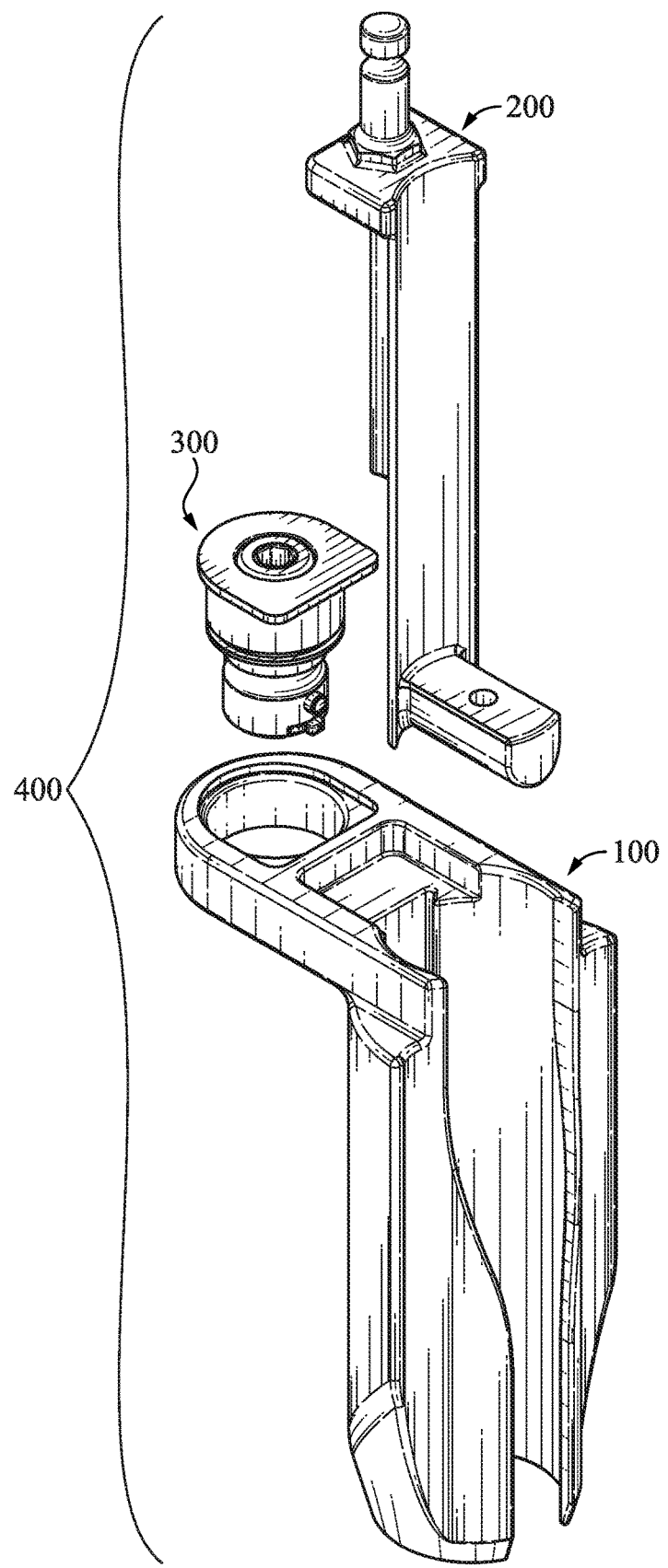
FIG. 2 is an exploded perspective view of the inverted pedicle retractor assembly of FIG. 1.
Figure 3:
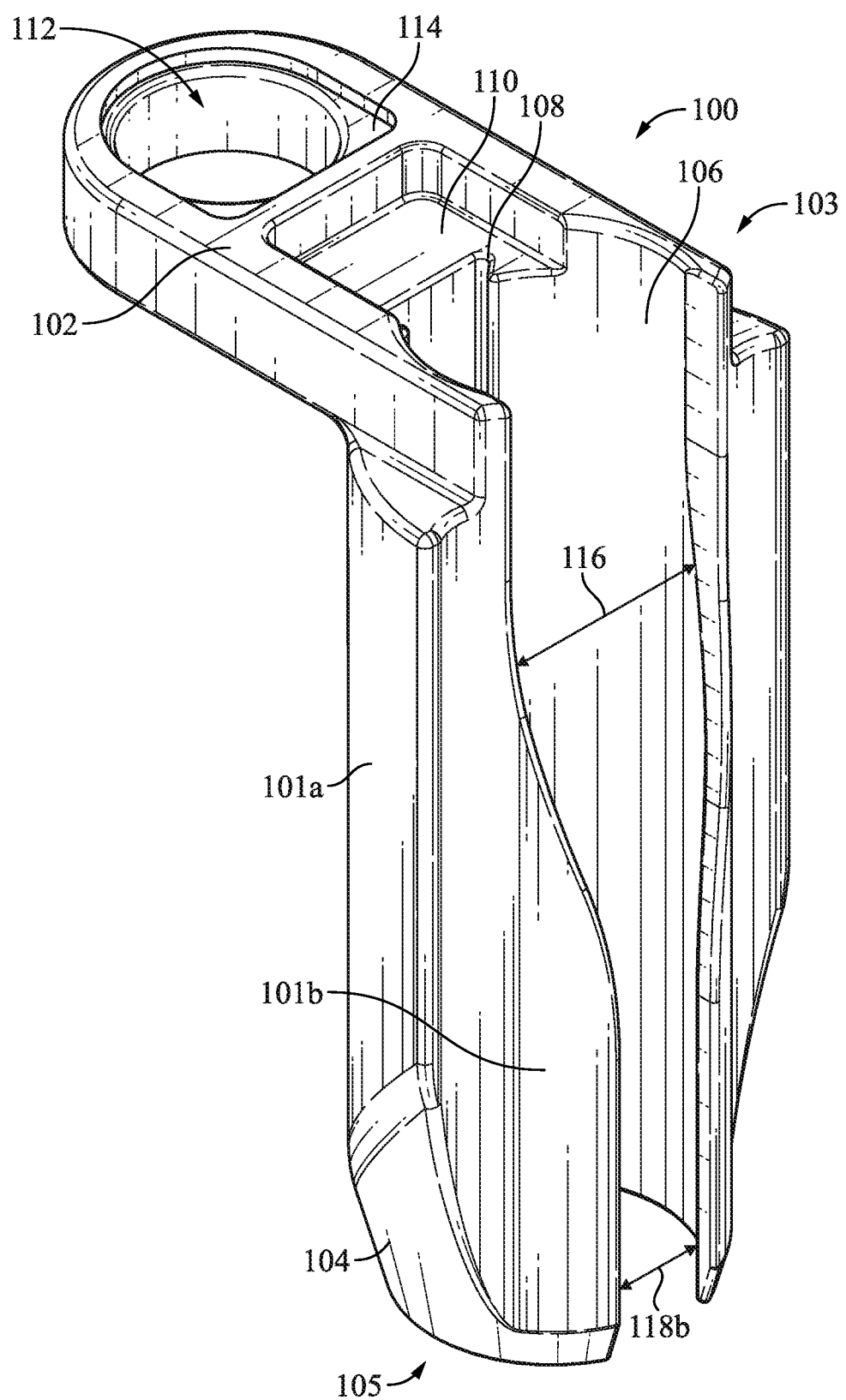
FIG. 3 is a perspective view of a retractor blade body of the inverted pedicle retractor assembly FIG. 1, in accordance with embodiments disclosed herein.
Figure 5:
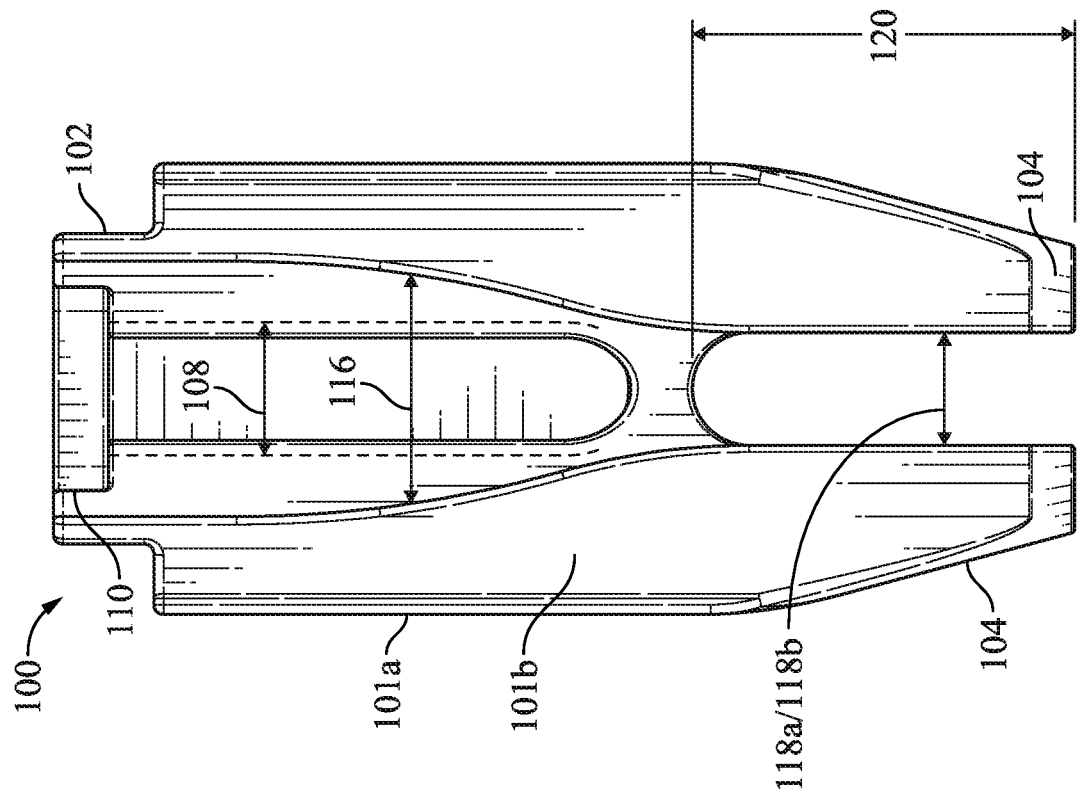
FIG. 5 is a rear view of the retractor blade body of FIG. 3.
Figure 4:
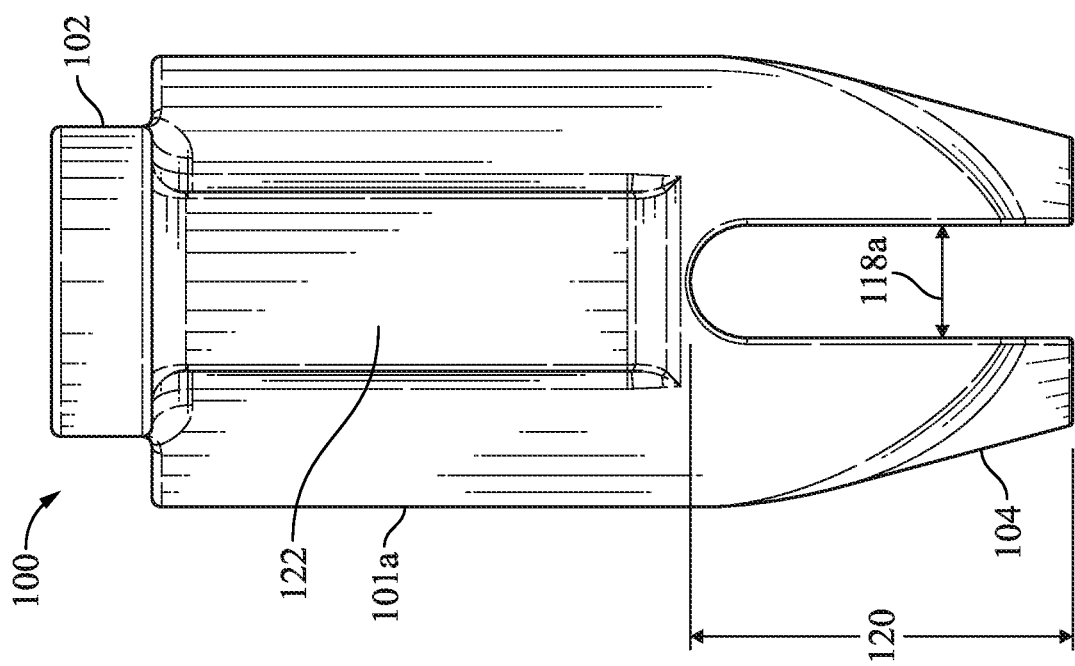
FIG. 4 is a front view of the retractor blade body of FIG. 3.
Figure 6:
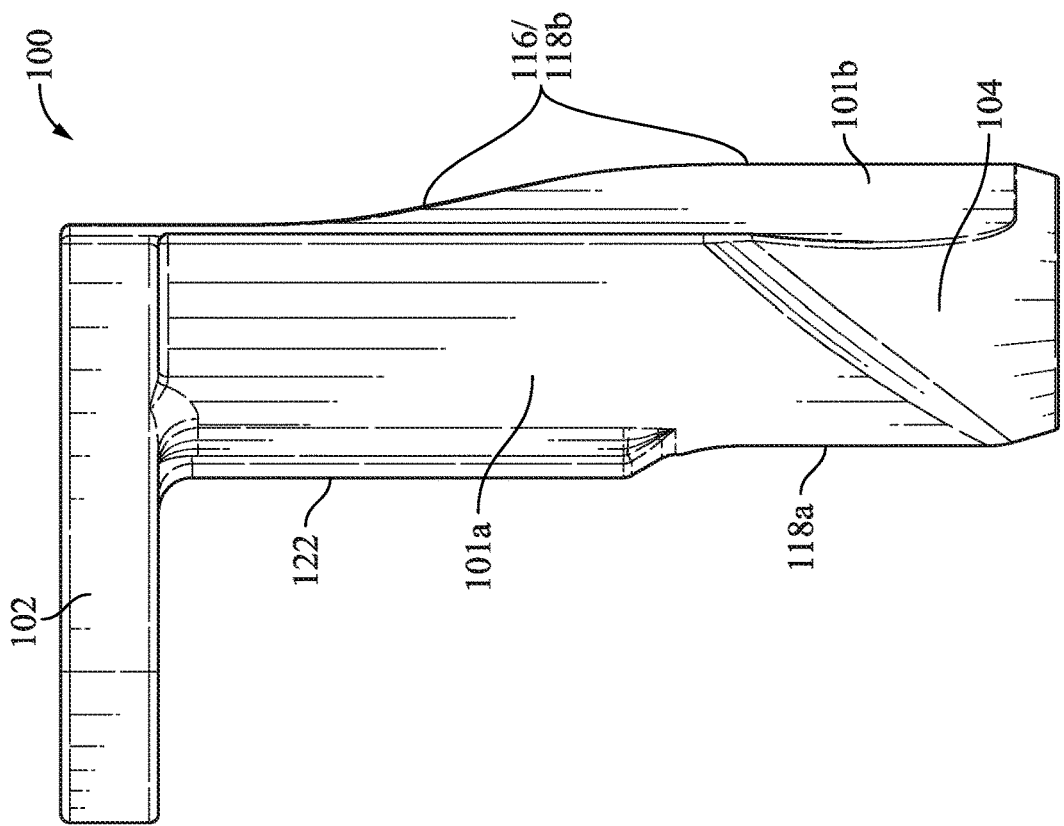
FIG. 6 is a left side view of the retractor blade body of FIG. 3.
Figure 7:
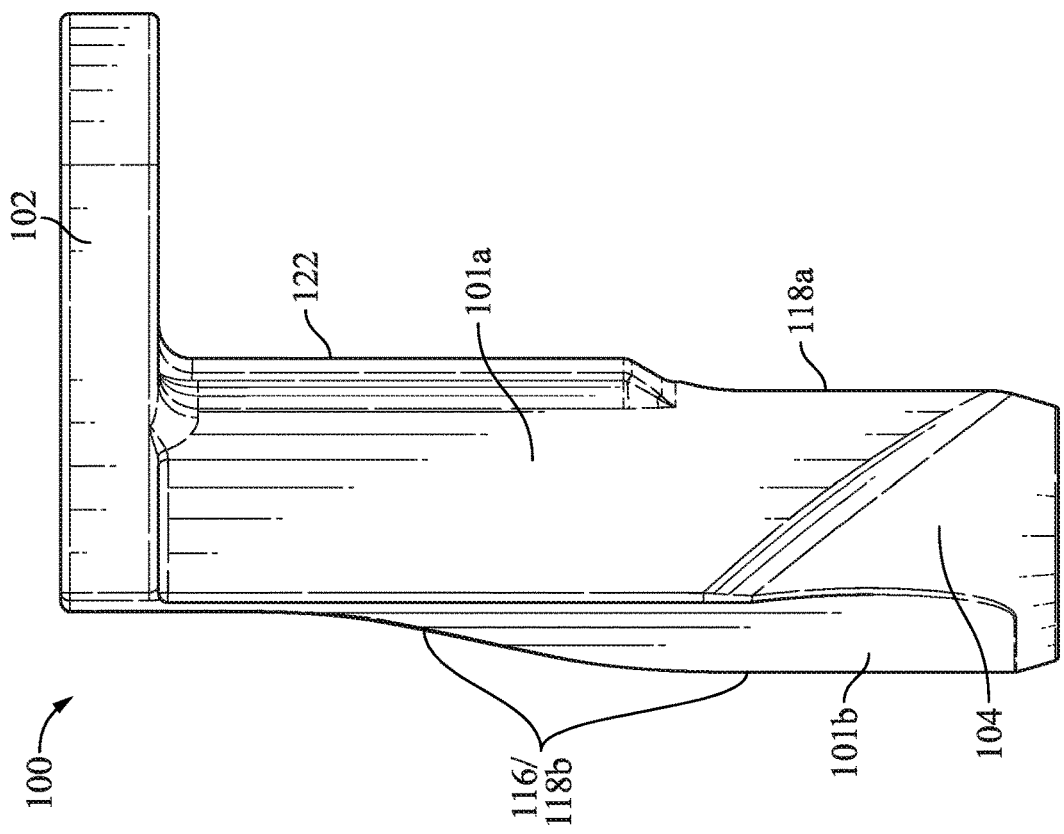
FIG. 7 is a right-side view of the retractor blade body of FIG. 3.
Figure 9:
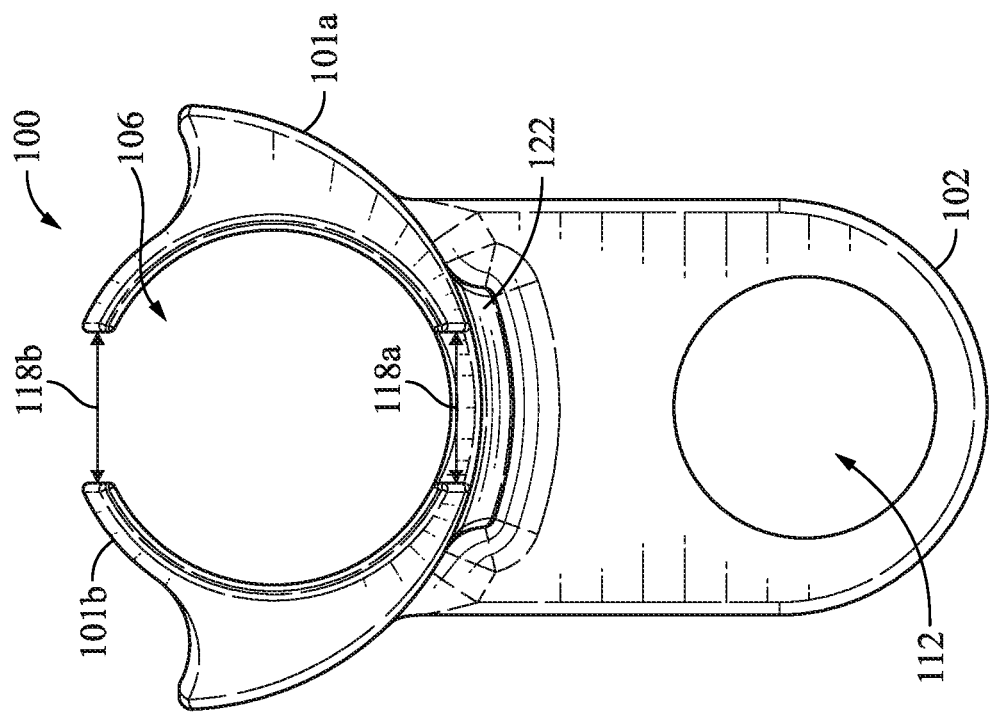
FIG. 9 is a bottom view of the retractor blade body of FIG. 3.
Figure 8:
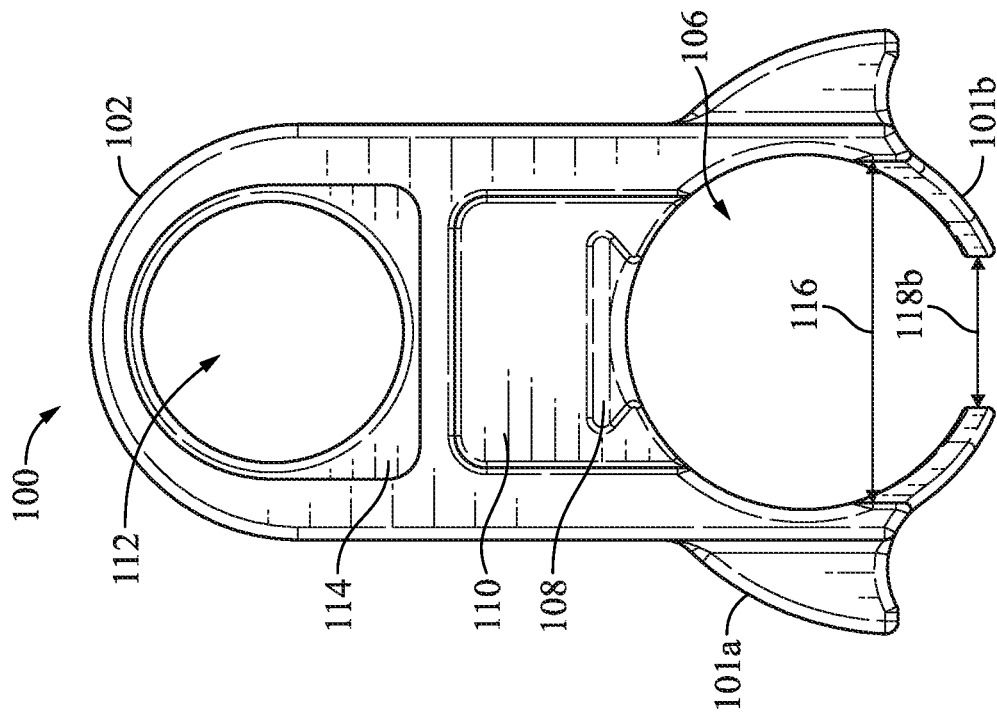
FIG. 8 is a top view of the retractor blade body of FIG. 3.
Figure 10:
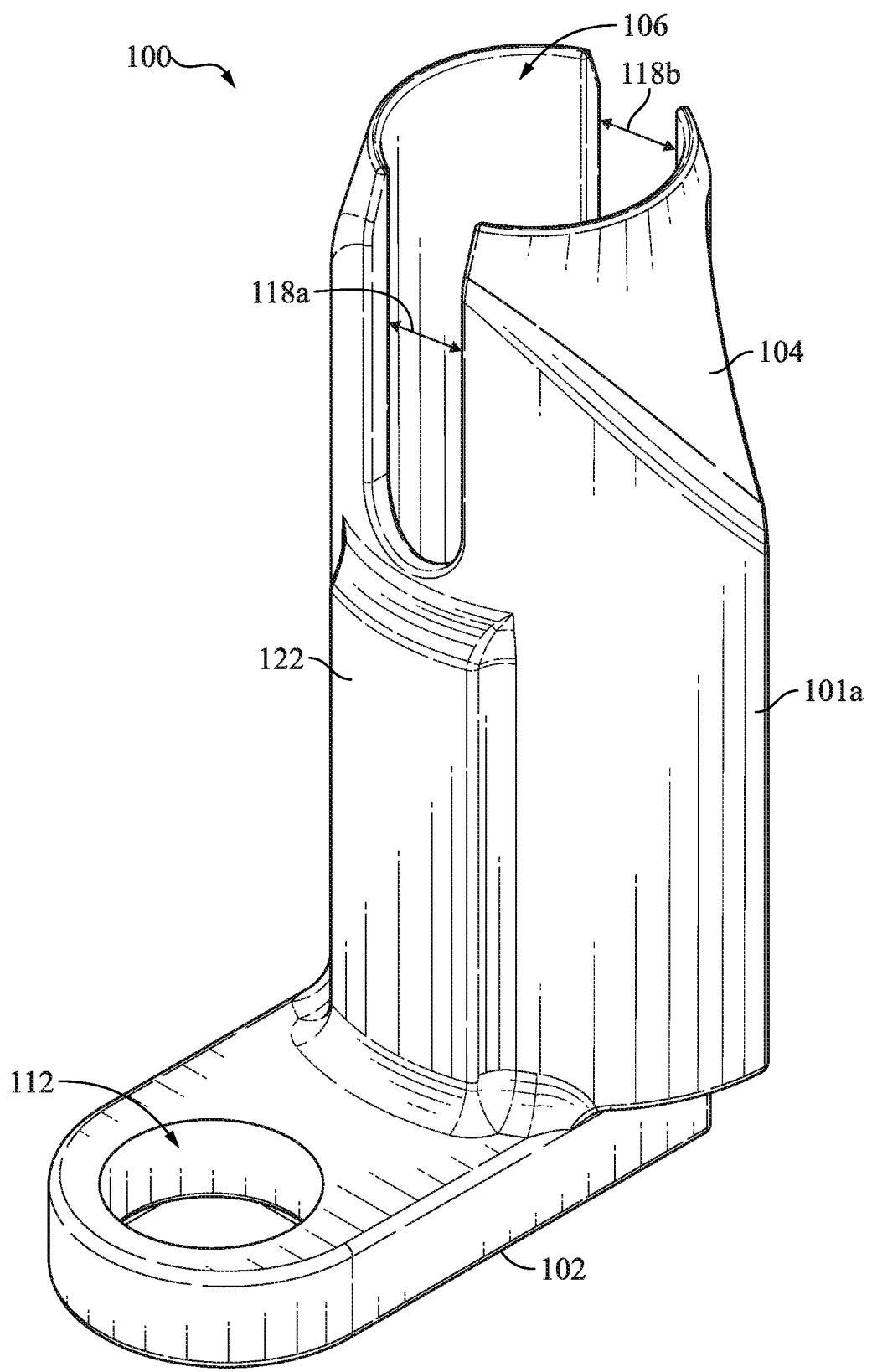
FIG. 10 is a bottom (front) perspective view of the retractor blade body of FIG. 3.
Figure 11:
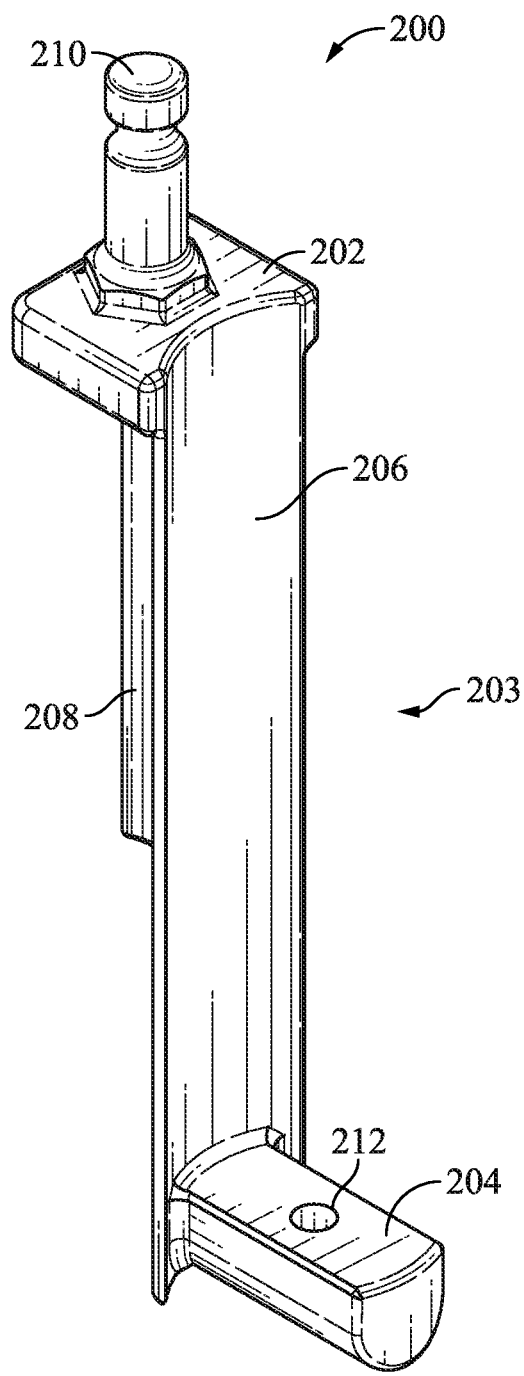
FIG. 11 is a top perspective view of the locking shim or "L" bracket, in accordance with embodiments disclosed herein.
Figure 16:
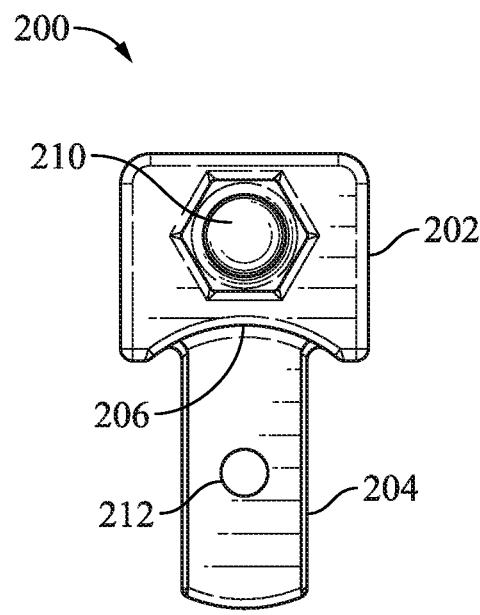
FIG. 16 is a top view of the locking shim of FIG. 11.
Figure 17:
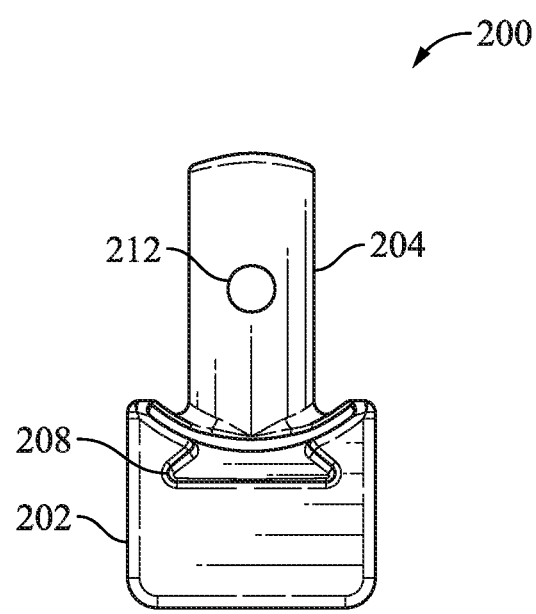
FIG. 17 is a bottom view of the locking shim of FIG. 11.
Figure 18:
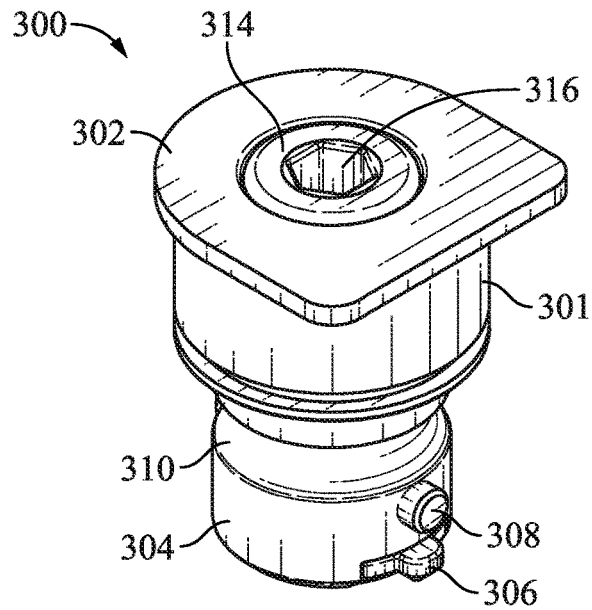
FIG. 18 is a top perspective view of the connection post sub-assembly, in accordance with embodiments disclosed herein.
Figure 19:
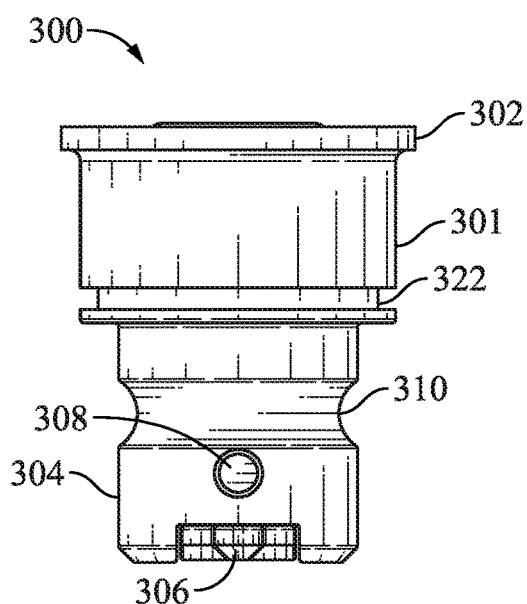
FIG. 19 is a front view of the connection post sub-assembly of FIG. 18.
Figure 20:
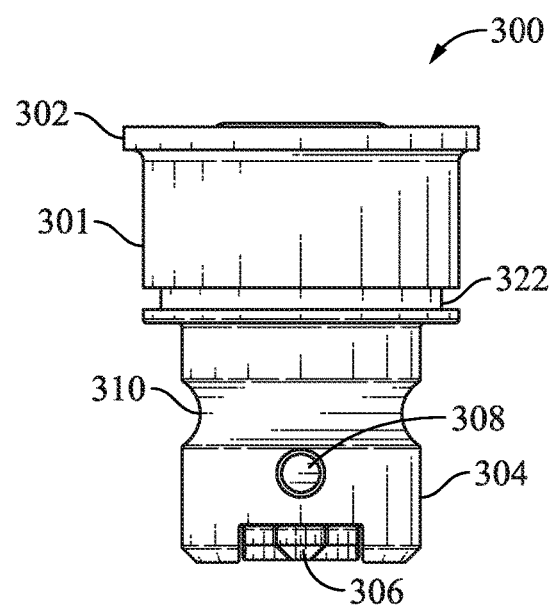
FIG. 20 is a rear view of the connection post sub-assembly of FIG. 18.
Figure 21:
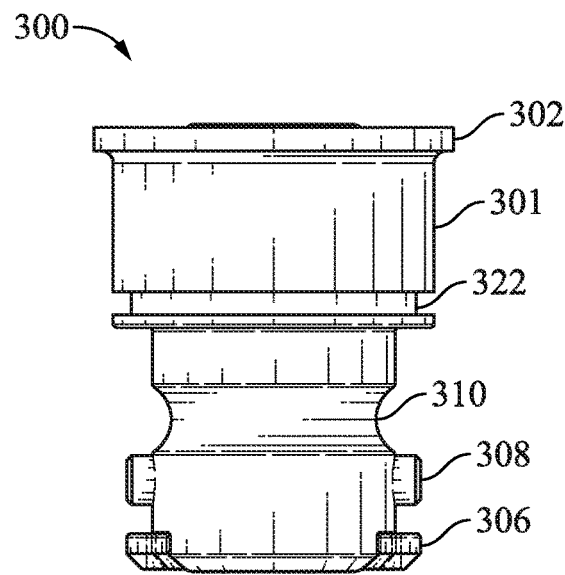
FIG. 21 is a left side view of the connection post sub-assembly of FIG. 18.
Figure 22:
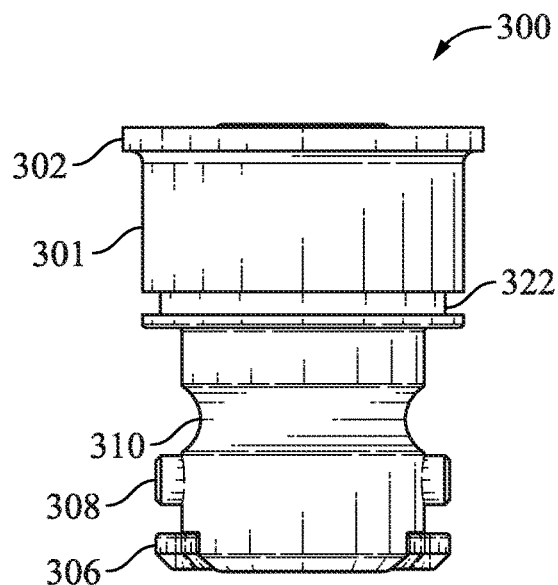
FIG. 22 is a right-side view of the connection post sub-assembly of FIG. 18.
Figure 23:
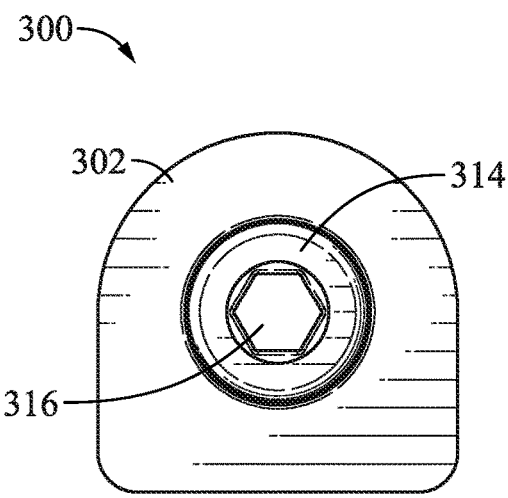
FIG. 23 is a top view of the connection post sub-assembly of FIG. 18.
Figure 24:
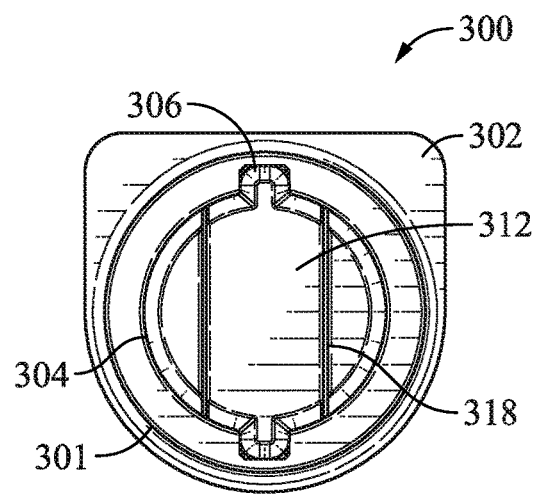
FIG. 24 is a bottom view of the connection post sub-assembly of FIG. 18.
Figure 25:
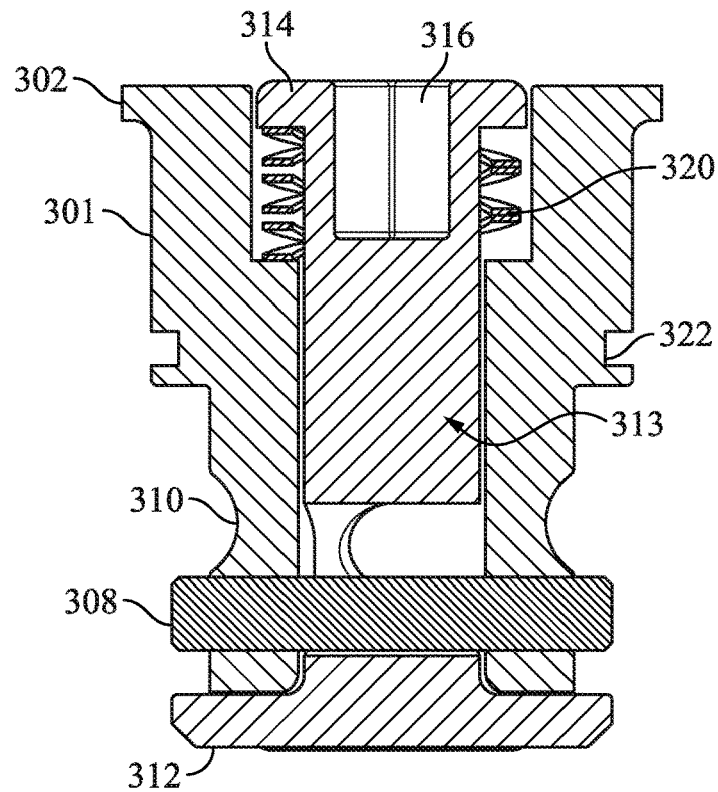
FIG. 25 is a cross-section view of the connection post sub-assembly of FIG. 18.
Figure 26:
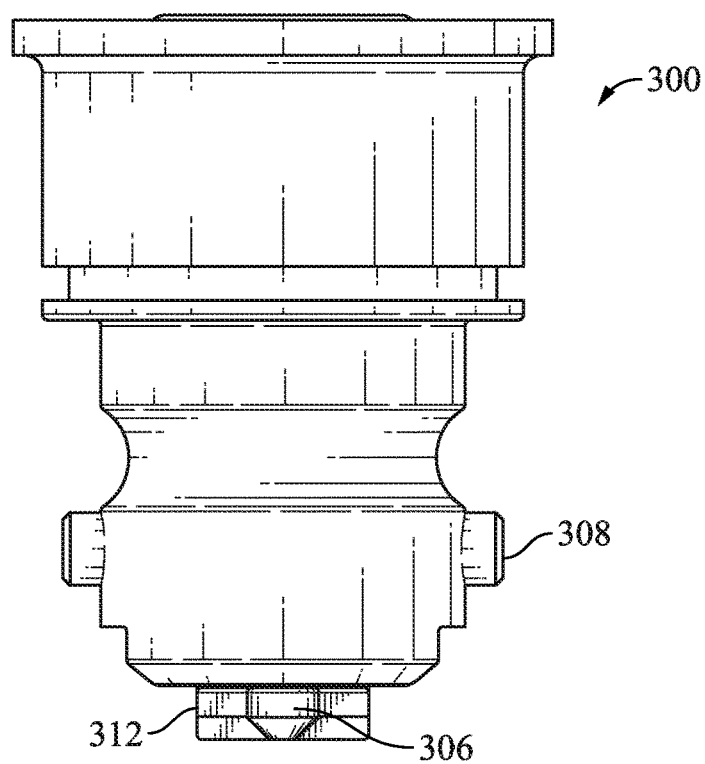
FIG. 26 is a view of the connection post sub-assembly with the extended and rotated T-bar locking feature, in accordance with embodiments disclosed herein.

As shown in FIGS. 11-17, the system includes a first and a second locking shim 200; wherein each locking shim 200 comprises a leg 203 having an inside diametral portion 206 and an exterior male dovetail capture feature 208, a distal L-shaped foot 204 having a guidewire hole 212 therethrough, an opposing proximal top flange 202 projecting away from the distal L-shaped foot and an inserter post 210 projecting proximally from the top flange, wherein each said retractor blade body and distal L-shaped foot 204 is configured for placement over and onto an extended tulip of a first and a second pedicle screw 15 as illustrated in FIG. 1B, wherein the locking shim is configured for removable locking placement between the extended tangs of a pedicle screw tower of each of a first and a second pedicle screw, within each diametral retractor blade body, and wherein each pedicle screw is pre-positioned in a pair of adjacent caudal 20 and cephalad 30 vertebrae on the same side of the spine and configured for distracting the vertebrae.

In some embodiments, the proximal top flange 202 of each locking shim 200 comprises an attachment feature 210 configured to receive an inserter/extractor tool (not shown), wherein said attachment feature comprises: a threaded hole; a post; a threaded post; a snap-detent; a bayonet attachment; or a compression-type fitting. As noted above, in some embodiments, the distal L-shaped foot 204 of the locking shim comprises a guidewire hole 212 therethrough, which can be utilized to precisely guide the placement of the locking shim and or entire screw tower assembly 400 over a guidewire that was radiographically guided and placed in the pedicle to pilot the placement of a pedicle screw. Following the guidewire with the guidewire hole in the distal L-shaped foot of the locking shim would precisely place the locking shim between the tulip of the pedicle screw when the screw capture or tulip for each pedicle screw is typically 25 mm or more below the surface of the skin.

Figure 27:
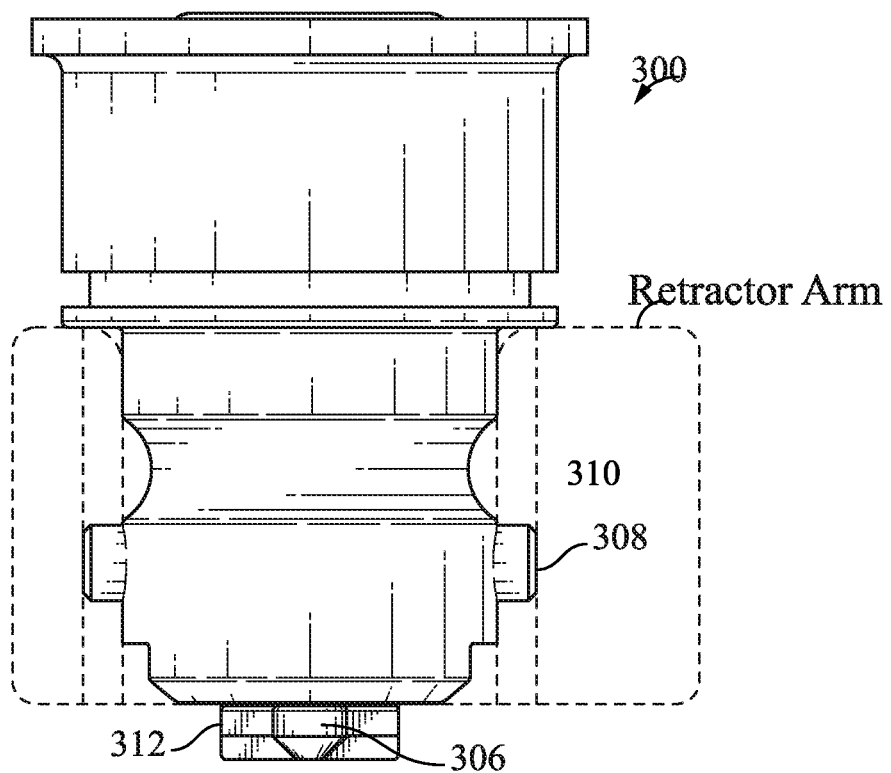
FIG. 27 is an alternative view of the connection post sub-assembly in FIG. 26, with attached handles or connecting arms from a distractor shown in abstract, in accordance with embodiments disclosed herein.

Referring now to FIGS. 18-25, the system comprises a unique inverted connection post sub-assembly 300 configured for compression or interference fit attachment to the proximal shoulder of the retractor blade body 100, via the thru-hole 112, having the stepped counter-seat 114. The inverted connection post sub-assembly 300 comprises a superior capture shoulder flange 302 and a major outside diameter 301 configured for compression or interference fit with the connection post capture diameter 112 and shoulder capture 114 of the retractor blade shoulder 102. The inverted connection post sub-assembly 300 further comprises an internal spring-loaded mechanism configured to pilot and lock the pedicle screw-mounted retractor blade bodies onto a universal-style spinal retractor or retractor handle. The mechanism comprises a T-bar connection rod 313 having an Allen head 314 and Allen socket 316 and a compression spring 320 resting on an internal shoulder of the post sub-assembly. The base of the T-bar connection rod comprises a connection post T-bar 312 configured with projection tangs 306 intended to guide and lock into a mating T-slot of a universal-style spinal retractor or retractor handle, as illustrated in FIG. 1B and FIG. 27. Additionally, the connection post sub-assembly comprises a location pin 308, configured to help guide the connection post into and through the mating T-slot of the universal-style spinal retractor or retractor handle. Finally, each inverted connection post sub-assembly comprises an optional c-clip capture ring groove 322 to allow for optional slip fit assembly to the retractor blade shoulder 102 and an O-ring groove 310 to provide a positive feedback capture mechanism when assembled to the universal-style spinal retractor or retractor handle.

In some embodiments of system 10, the distracting of the vertebrae 20/30 with the pedicle screws is performed with the retractor blade screw tower assemblies 400 securely positioned over and locked onto the pedicle screws 15 while maintaining the pedicle screws parallel with the tubes during a distraction maneuver with a pedicle-based retractor attached to the distally extending post sub-assemblies 300. During operation, the pedicle screw-mounted retractor system 10 is removably assembled with a commercially available universal-style spinal retractor or retractor handle, in which an arm of the retractor or handle having a mating capture hole and alignment groove is moved into position beneath the unique inverted connection post sub-assembly 300 of the pedicle screw-mounted retractor system 10 and aligned with the locating pins 308 and T-bar tabs 306. At this point the user then applies an Allen wrench to depress the compression spring 320 and T-bar connection rod 313 having the Allen head cap 314 and Allen socket 316. The spinal retractor arm or retractor handle is then pulled up by the user until fully engaged onto the inverted connection post sub-assembly. In this manner, the bending stresses that might otherwise be transmitted to the pedicle screw or tulip by pushing down on the spinal screw are averted, thus mitigating the potential for snapping or breaking the tulip off of the spinal screw 15. Finally, a user then applies a 90-degree twisting motion to the Allen head to twist the mechanism and T-bar tabs 306 until they can capture a solid surface of the spinal retractor arm or retractor handle beyond the alignment groove.

As illustrated in FIG. 1B and FIG. 27, once the T-bar tabs 306 of the inverted connection post sub-assembly 300 are fully engaged in the mating hole(s) of the retractor arm(s) or handle(s), the universal-style spinal retractor or retractor handle can be fully engaged to spread or separate the adjoining vertebrae 20, 30 to provide the necessary room and visualization needed by the surgeon to perform the procedure and deliver spinal rods.

Referring now to FIG. 28 and FIG. 29, in some embodiments, the system provides at least two dilators designed to uniquely separate and open MIS incisions in preparation for insertion of the pedicle screw-mounted retractor blade body following the placement of pedicle screws, which are usually inserted into the spinal pedicles under radiographic guidance.

In some embodiments, the system further comprises a set of MIS spinal dilators 500, 510 sized to dilate an incision between the pair of pedicle screws. In such embodiments, each retractor blade body of the pedicle screw-mounted retractor system is configured to pass over and attach onto each pedicle screw tower positioned in an adjacent vertebra and the dilators positioned therebetween are configured to increase the size of an MIS surgical working portal therebetween. In some embodiments, the set of MIS spinal dilators comprises: a flat "tongue depressor" dilator 500 comprising a tapered distal end 504, and a "peanut" dilator 510, configured with a slidably corresponding/matching through-slot 511 within its longitudinal length configured to allow the peanut dilator 510 to slide over the flat tongue depressor dilator 500, and a tapered distal end 514. During use, once in place, the flat tongue depressor dilator can be extracted, leaving the peanut dilator in place. The peanut dilator 510 can then be twisted to engage the concave sides 512 of the peanut dilator instead of the parallel sides 513, to push tissue out of the way and expand the MIS would site. Oftentimes, surgeons will elect to utilize additional commercially available tubular expanding diametral dilators (not shown) to further enlarge the tissues surrounding the MIS wound area to enhance their view or provide larger ports for delivery of instruments or removal of tissues.

In various embodiments, a method of distracting a pair of adjacent vertebrae for a TLIF procedure is provided. In some embodiments, the method comprises creating a MIS incision for a central working MIS portal for a spinal TLIF procedure; inserting dilators 500, 510 in the central working MIS portal to expand and open soft tissue to visualize and verify position and anatomy; and inserting a pair of pedicle screws 15 with threaded towers and/or extended tangs, one in each pedicle, in adjacent caudal 20 and cephalad 30 vertebra, on the ipsilateral side of the spine where the TLIF procedure is being performed. In some embodiments, the central working portal of each retractor blade tube has at least a 20 mm diameter in each of the first and second bodies. In some embodiments, the diameter is from 10-200 mm, 15-190 mm, 19-185 mm, 25 mm, 30 mm, 35 mm, 50 mm, etc. The endpoints of each range are included in the range, and any intervening number within the range is intended to be used as an endpoint for any unrecited subrange (e.g., the range 10-200 mm encompasses 10 mm and 200 mm, as well as 20-180 mm and 55-155 mm).

In some embodiments, the method further comprises providing a first and a second pedicle screw-mounted retractor blade body 100 and placing each retractor blade body over and onto each of the pedicle screw towers, flush to the pedicle. In such embodiments, each retractor blade tube 101a, 101b comprises an inside diameter 106 with a retaining alignment groove 108, a first partially offset non-concentric outside diameter 101a and a second partially concentric outside diameter 101b, said second partially concentric outside diameter being configured with a tapered visualization slot 116, 118b extending from a proximal end 103 to a distal end 105, said visualization slots on the back side of each first and a second pedicle screw-mounted retractor blade body positioned diametrically facing each other when the pair of retractor blade tubes are placed over the pedicle screws, and each retractor blade body having a proximal end flange 102 extending perpendicular on a side opposite the visualization slot, with an inverted post sub-assembly 300 extending distally therefrom and positioned diametrically opposed to each other (on the front sides of the retractor blade bodies) when the retractor blade bodies are placed over the pedicle screws, and wherein each retractor blade tube further comprises a second distal slot 118a on a diametral side (front side) opposite the visualization slot, along the distal half of the retractor blade tube comprising the first partially offset non-concentric outside diameter 101a.

In some embodiments, the method further comprises inserting a locking shim 200 with a mating retaining alignment projection 208 on the leg 203 of the shim on the side opposite the inside diametral portion 206 of the shim, within the retractor blade tube 106 in the retainment slot 108. In such embodiments, a protruding distal foot 204 of said locking shim is configured for placement between extended threaded towers or extended tangs of each tower (not shown) of each of the first and a second pedicle screw 15. In some embodiments, the method further comprises inserting a pedicle set screw (not shown) into each of the extended threaded towers or extended tangs of each of the first and a second pedicle screws, removably locking each locking shim in place within each pedicle screw tower, securing the retractor blade assembly to each pre-positioned ipsilateral pedicle screw, forming a retractor blade screw tower assembly 400.

In some embodiments, the method further comprises attaching a commercially available spinal pedicle-based retractor or handle to each distally extending inverted post 300; performing a distraction maneuver, wherein the distraction of the vertebrae spacing occurs when the cylindrical retractor blade bodies are distracted in caudal and cephalad directions; and removing the dilators, leaving the retractor blade bodies in place to visualize through the central working MIS portals and back-side visualization slots 116, 118*b* to verify the position and anatomy.

In some embodiments, at any time following the insertion of the pedicle screws on the ipsilateral side of the spine, the method further comprises inserting a second pair of pedicle screws with threaded towers or extended tops or tangs with threaded posts, one in each pedicle, in adjacent caudal and cephalad vertebra, on the contralateral side of the spine where the TLIF procedure is being performed. In some embodiments, following the distraction maneuver, the method further comprises a TLIF procedure can be performed.

In some embodiments, following the TLIF procedure, the method further comprises releasing the distraction maneuver with the pedicle-based retractor to allow compression of a TLIF-treated disc space; removing the set screws from each of the first and a second pedicle screws; removing the locking shims 200 from each of the first and a second retractor blade screw tower assemblies 400; inserting spinal rods through the second distal slots 118*a* of the pedicle screw towers between the adjacent caudal and cephalad vertebra on the ipsilateral side of the spine; inserting a pedicle set screw into each of the extended threaded tangs of each of the first and a second pedicle screws on the ipsilateral side of the spine, locking each spinal rod in place within each pedicle screw; inserting spinal rods between the adjacent caudal and cephalad vertebra on the contralateral side of the spine; and inserting a pedicle set screw into each of the extended threaded tangs of each of the first and a second pedicle screws on the contralateral side of the spine, locking each spinal rod in place within each pedicle screw In some embodiments, at any time following the releasing the distraction maneuver, the method further comprises removing the pedicle-based retractor from each inverted connection post sub-assembly of each retractor blade body; and removing each retractor blade body from the pedicle screws in the adjacent caudal and cephalad vertebra.

In various embodiments, a pedicle screw-mounted retractor system is provided. The system comprises a first and a second pedicle screw-mounted retractor blade body having a proximal and distal end, a proximal shoulder, an inside diameter, a first partially offset non-concentric outside diameter and a second partially concentric outside diameter; and a first and a second locking shim; wherein each retractor blade body comprises a longitudinal diametral tube configured with a proximal opening a distal opening and through bore, wherein each locking shim comprises a leg, a distal L-shaped foot with a centrally positioned guidewire hole, an opposing proximal top flange projecting away from the distal L-shaped foot, wherein each said retractor blade body is configured for placement over and onto an extended tulip of a first and a second pedicle screw, wherein the locking shim, with the centrally positioned guidewire hole in the L-shaped foot, is configured for guiding a partially assembled retractor blade assembly over a pre-positioned guidewire that was used to position a canulated pedicle screw in the facet of a vertebrae, wherein, once positioned within the tulip of the pre-positioned pedicle screw, each said locking shim is configured for removable locking placement with a set screw between the extended tangs of said tulip of each of the first and a second pedicle screw, within each diametral retractor blade tube, and wherein each pedicle screw is pre-positioned in a pair of adjacent caudal and cephalad vertebrae on the same side of the spine and configured for distracting the vertebrae.

In some embodiments, the pedicle screw-mounted retractor system is configured for placement on the ipsilateral side of the spine where a TLIF procedure is being performed. In some embodiments, the guidewire hole in the L-shaped foot of the locking shim is approximately 3.2 mm in diameter.

In some embodiments, the system further comprises a proximal end flange extending perpendicularly on one side of each retractor blade body, comprising a first receptacle configured to receive the proximal top flange of the locking shim and a post sub-assembly extending distally from the second receptacle, wherein each said post sub-assembly is configured to lockably receive a handle or a mounting arm of a spinal joint retractor.

In some embodiments, the distally extending post sub-assembly comprises a spring-loaded mechanism comprising a locking feature configured to extend through and rotationally lock onto or into a mating receiving aperture of a handle or a mounting arm of a spinal joint retractor to temporarily hold the pedicle screw-mounted retractor blade body for a retraction step in a spinal procedure. In some embodiments of the distally extending post sub-assembly, the locking feature comprises a T-bar, a hook, an L-shaped foot, a bayonet connection or a ball detent.

As used herein, and unless otherwise specified, the terms "connection device," "connector" and "attachment coupling" mean a device intended for connecting parts together or for the pairing of two items; a device that serves to connect the ends of adjacent parts or objects.

As used herein, and unless otherwise specified, the terms "snap-on" or "detent" mean a type of connection mechanism configured for removeable attachment of a mating component such as a handle, wherein the connection mechanism commonly comprises a groove and inset split washer, "O-ring", or similar retaining mechanism that allows a mating sleeve or device commonly configured with a holed-connection to slide over the snap-on or detent feature and be temporarily held in place. Alternatively, the snap-on or detent feature can be configured within a hole, as an inset groove, again with an inset split washer, "O-ring", or similar retaining mechanism that would temporarily capture and hold a mating post when inserted therein.

As used herein, and unless otherwise specified, the term "caudal" or "caudad" is used as an anatomic directional term that means "towards the tail." At the level of the spinal cord, caudal indicate the direction that points down, or towards the feet; in the opposite direction from cephalad.

As used herein, and unless otherwise specified, the term "cephalad" or "cephalic" is used as an anatomic directional term that means "toward the head"; forward in the long axis of the body; in the opposite direction from caudad. In man it is upward, and in most animals forward; but in any case it is used without reference to the posture of the body. Cephalic is synonymous with cranial, relating to the cranium or head.

As used herein, and unless otherwise specified, the term "retractor," "retractor blade," "retractor blade tube," "retractor blade body," or "crew tower assembly" refers to a surgical instrument used to separate the edges of a surgical incision or wound, or to hold back underlying organs and tissues so that body parts under the incision may be accessed, particularly as it relates to MIS surgery of the spine. The term retractor usually describes a handheld tool, commonly a stainless-steel tool, possessing a curved, hooked, or angled blade and fitted with a comfortable handle, that when placed in a wound, maintains the desired position of a given region of tissue. These retractors may be handheld, clamped in place, or suspended at the end of a robotic arm.

In some embodiments, the retractors have features resembling common surgical retractors, as well as tubular dilators, which are commonly used in spinal MIS (Minimally Invasive Surgery) procedures. Tubular dilators are inserted into incisions just a few centimeters in length. These dilators are commonly provided in circumscribed sets of tubes having increasing diameters of tubes designed to slide over one another and that create channels through muscle and other tissue, down to the area of interest. Instead of cutting the muscles and tissues, the dilators move them aside. A final tube called a retractor fits over the dilators. Its function is to hold the tissues apart during surgery. Once the retractor is in place, the dilators can be removed. The instruments used to perform MIS spinal procedures typically pass down through the retractors to reach the spine. Any material removed during surgery (for example, disc material or bone) is extracted up through the retractors. Retractors can also be self-retaining and not need to be held once inserted by having two or more opposing blades or hooks which are separated via spring, ratchet, worm gear, a ring or other method. In some embodiments, for specialized situations such as spinal surgery, some retractors have been fitted both with suction and with fiberoptic lights to keep a surgical wound dry and illuminated. The screw-mounted retractor blades described in this system serve all of these functions and more, with interlocking features and fewer components.

As used herein, and unless otherwise specified, the term "distraction" means separation of joint surfaces without rupture of their binding ligaments and without displacement, or a method of straightening a spinal column by the forces of axial tension pulling on the joint surfaces.

As used herein, and unless otherwise specified, the term "dilator" or "dilate" refers to a surgical instrument or medical implement used to induce dilation, that is, to expand an opening or passage such as the incision between the pair of pedicle screws; and configured to increase the size of an MIS (Minimally Invasive Surgery) surgical working portal, wherein a unique set of MIS spinal dilators described herein comprises: a flat "tongue depressor" dilator, and a "peanut" dilator, configured with a slidably matching through-slot within its longitudinal length configured to allow the peanut dilator to slide over the flat tongue depressor dilator.

As used herein, and unless otherwise specified, the term "front side" typically refers to either the cephalad or caudal side of an instrument or pedicle retractor blade, since these instruments can be applied on either side or end of a vertebra or a wound. As used herein, and unless otherwise specified, the term "rear side" or "back side" typically refers to side of an instrument or pedicle retractor blade that is between the cephalad and caudal vertebra being treated, wherein the "rear side" or "back side" of a retractor blade would then be facing the "rear side" or "back side" of an opposing retractor blade.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure, in accordance with the claims. It should be understood that various alternatives to the embodiments of the disclosure described herein may be employed in practicing the embodiments of the disclosure.

What is claimed is:

1. A pedicle screw-mounted retractor system, comprising:
   a first and a second retractor blade body having a proximal and distal end, a proximal shoulder, an inside diameter, a first partially offset non-concentric outside diameter and a second partially concentric outside diameter; and
   a first and a second locking shim;
   wherein each of the first and second locking shim comprises a leg, a distal L-shaped foot, an opposing proximal top flange projecting away from the distal L-shaped foot, and
   wherein each of the first and second locking shim is configured for removable locking placement between two or more tangs of a pedicle screw tower of each of the first and a second pedicle screw, within each diametral retractor blade body;
   a proximal end flange extending perpendicularly on one side of each retractor blade body, comprising a first receptacle configured to receive the proximal top flange of the locking shim and a second receptacle to receive a post sub-assembly; and
   a post sub-assembly extending distally from the second receptacle,
   wherein each said post sub-assembly is configured to lockably receive a handle or a mounting arm of a spinal joint retractor,
   wherein each of the first and second retractor blade body comprises a longitudinal diametral tube configured with a proximal opening, a distal opening, and through bore,
   wherein each of the first and second retractor blade body is configured for placement over and onto an extended tulip of a first and a second pedicle screw, each pre-positioned in a pair of adjacent caudal and cephalad vertebrae on a same side of a spine and configured for distracting the vertebrae, and
   wherein each retractor blade body further comprises at least one visualization slot through one side of the retractor blade body, said at least one visualization slot positioned diametrically opposite the side having the proximal end flange.

2. The pedicle screw-mounted retractor system of claim 1, wherein each retractor blade body further comprises an alignment groove on the inside diameter configured to receive a mating alignment projection on the leg of each of the locking shims, forming a tower assembly when each locking shim is inserted into each retractor blade body.

3. The pedicle screw-mounted retractor system of claim 2, wherein the alignment groove on the inside diameter each retractor blade body is configured to be:
   av-groove;
   an undercut groove;

a dovetail;
a through dovetail;
a half-blind dovetail; or
a sliding dovetail; and
  wherein the alignment projection on the leg of each of the locking shims is configured to slidably mate with the alignment groove and prevent disassociation of the shim from the inside diameter of the retractor blade body.

4. The pedicle screw-mounted retractor system of claim 3, wherein the proximal top flange of each locking shim comprises an attachment feature configured to receive an inserter/extractor tool, wherein said attachment feature comprises:
a threaded hole;
a post;
a threaded post;
a snap-detent;
a bayonet attachment; or a compression-type fitting.

5. The pedicle screw-mounted retractor system of claim 1, wherein the locking shim can be releasably locked in place on each pedicle screw tower, forming a retractor blade screw tower assembly.

6. The pedicle screw-mounted retractor system of claim 1, wherein each retractor blade body further comprises an additional slot, on a side diametrically opposed to the at least one visualization slot, on the same side as the proximal end flange, along the distal half of the retractor blade body and configured to accommodate the passage of a spinal connecting rod therethrough.

7. The pedicle screw-mounted retractor system of claim 6, wherein the additional slot extends from the distal end of each diametral retractor blade body to a point 50% of the length to the proximal end.

8. The pedicle screw-mounted retractor system of claim 7, wherein each retractor blade body further comprises a tapered exterior configuration at or about the distal end of a tube body.

9. The pedicle screw-mounted retractor system of claim 1, wherein the distracting of the vertebrae with the pedicle screws is performed with the retractor blade screw tower assemblies securely positioned over and locked onto the pedicle screws while maintaining the pedicle screws parallel with the tubes during a distraction maneuver with a pedicle-based retractor attached to the distally extending post sub-assemblies.

10. The pedicle screw-mounted retractor system of claim 1, wherein the first partially offset non-concentric outside diameter comprises an approximately semi-circular non-concentric offset diameter for one half of the outside diameter and the second partially concentric outside diameter comprises an approximately semi-circular concentric outside diameter for the other half of the outside diameter.

11. The pedicle screw-mounted retractor system of claim 1, wherein each said distally extending post sub-assembly further comprises a spring-loaded locking mechanism for engaging the handle or the mounting arm of a spinal joint retractor; and
  wherein said spring-loaded locking mechanism is engaged with an engagement driver to activate and release the mechanism.

12. The pedicle screw-mounted retractor system of claim 1, wherein the proximal end flange further comprises an attachment feature configured to receive an inserter/extractor tool,
  wherein said attachment feature comprises:
  a threaded hole;
  a post;
  a threaded post;
  a snap-detent;
  a bayonet attachment; or
  a compression-type fitting.

13. The pedicle screw-mounted retractor system of claim 1, further comprising:
  a set of MIS spinal dilators sized to dilate an incision between the pair of pedicle screws,
  wherein each retractor blade body of the pedicle screw-mounted retractor system is configured to pass over and attach onto each pedicle screw tower positioned in the adjacent vertebrae and the dilators positioned therebetween configured to increase the size of an MIS surgical working portal therebetween,
  wherein the set of MIS spinal dilators comprises:
  a flat tongue depressor dilator, and
  a peanut dilator, configured with a slidably matching through-slot within its longitudinal length configured to allow the peanut dilator to slide over the flat tongue depressor dilator.

14. A method of distracting a pair of adjacent vertebrae for a TLIF procedure, comprising:
  creating a MIS incision for a central working MIS portal for a spinal TLIF procedure; inserting dilators in the central working MIS portal to expand and open soft tissue to visualize and verify position and anatomy;
  inserting a pair of pedicle screws with threaded towers or extended tops or tangs with threaded posts, one in each pedicle, in adjacent caudal and cephalad vertebra, on the ipsilateral side of the spine where the TLIF procedure is being performed;
  providing a first and a second pedicle screw-mounted retractor blade body;
  placing each retractor blade body over and onto each of the pedicle screw towers, flush to the pedicle;
  wherein each retractor blade body comprises an inside diameter with a retaining alignment groove, a first partially offset non-concentric outside diameter and a second partially concentric outside diameter, said second partially concentric outside diameter being configured with a visualization slot extending from a proximal end to a distal end, said visualization slots positioned diametrically facing each other when the pair of retractor blade bodies are placed over the pedicle screws, and each retractor blade body having a proximal end flange extending perpendicular on a side opposite the visualization slot and comprising a first receptacle configured to receive a proximal top flange of a locking shim and a second receptacle to receive an inverted post sub-assembly extending distally therefrom and positioned diametrically opposed to each other when the retractor blade bodies are placed over the pedicle screws, and
  wherein each retractor blade body further comprises a second distal slot on a diametral side opposite the visualization slot, along the distal half of the retractor blade body comprising the first partially offset non-concentric outside diameter,
  inserting a locking shim with a mating retaining alignment projection within the retractor blade body, wherein a protruding distal L-shaped foot of said locking shim is configured for placement between extended threaded towers or extended tangs of each tower of each of the first and a second pedicle screw and wherein an opposing proximal top flange is projecting away from the distal L-shaped foot;

inserting a pedicle set screw into each of the extended threaded towers or extended tangs of each of the first and a second pedicle screws, removably locking each locking shim in place within each pedicle screw tower, securing the retractor blade assembly to each pre-positioned ipsilateral pedicle screw, forming a retractor blade screw tower assembly;

attaching a spinal pedicle-based retractor to each distally extending inverted post; performing a distraction maneuver;

wherein the distraction of the vertebrae spacing occurs when the cylindrical retractor blades are distracted in caudal and cephalad directions; and removing the dilators, leaving the retractor blades in place to visualize through the central working MIS portal to verify the position and anatomy.

15. The method of claim 14, wherein at any time following the insertion of the pedicle screws on the ipsilateral side of the spine, inserting a second pair of pedicle screws with threaded towers or extended tops or tangs with threaded posts, one in each pedicle, in adjacent caudal and cephalad vertebra, on the contralateral side of the spine where the TLIF procedure is being performed.

16. The method of claim 15, wherein following the distraction maneuver, a TLIF procedure can be performed.

17. The method of claim 16, wherein following the TLIF procedure:

releasing the distraction maneuver with the pedicle-based retractor to allow compression of a TLIF-treated disc space;

removing the set screws from each of the first and a second pedicle screws;

removing the locking shim from each of the first and a second retractor blade screw tower assembly;

inserting spinal rods through the second distal slots of the retractor blades and the pedicle screw towers between the adjacent caudal and cephalad vertebra on the ipsilateral side of the spine;

inserting a pedicle set screw into each of the extended threaded tangs of each of the first and a second pedicle screws on the ipsilateral side of the spine, locking each spinal rod in place within each pedicle screw;

inserting spinal rods between the adjacent caudal and cephalad vertebra on the contralateral side of the spine; and inserting a pedicle set screw into each of the extended threaded tangs of each of the first and a second pedicle screws on the contralateral side of the spine, locking each spinal rod in place within each pedicle screw.

18. The method of claim 17, wherein at any time following the releasing the distraction maneuver:

removing the pedicle-based retractor from each retractor blade; and removing each retractor blade from the pedicle screws in the adjacent caudal and cephalad vertebra.

* * * * *